(12) United States Patent
Ghesquiere et al.

(10) Patent No.: US 8,066,649 B2
(45) Date of Patent: Nov. 29, 2011

(54) INTEGRATED SENSOR FOR ANALYZING BIOLOGICAL SAMPLES

(75) Inventors: Alexander Ghesquiere, San Francisco, CA (US); Clive Nicholls, Stokenchurch (GB); John J Cabrall, Pleasanton, CA (US); Scott A Matula, Oakland, CA (US); Simon Andrew Hector, Swindon (GB); Javier Prieto, Boars Hill (GB); Adrian Petyt, Chipping Norton (GB); Geoffrey Roger Chambers, Berkhamsted (GB)

(73) Assignee: Abbott Diabetes Care Inc., Alameda, CA (US)

( * ) Notice: Subject to any disclaimer, the term of this patent is extended or adjusted under 35 U.S.C. 154(b) by 251 days.

(21) Appl. No.: 12/185,117

(22) Filed: Aug. 4, 2008

(65) Prior Publication Data

US 2009/0143700 A1 Jun. 4, 2009

Related U.S. Application Data

(62) Division of application No. 11/535,986, filed on Sep. 28, 2006.

(60) Provisional application No. 60/741,019, filed on Nov. 30, 2005.

(51) Int. Cl.
*A61B 5/00* (2006.01)
*A61B 17/14* (2006.01)
*A61B 17/32* (2006.01)

(52) U.S. Cl. .................. 600/583; 600/584; 606/181

(58) Field of Classification Search .................. 600/573, 600/583, 584; 606/181, 182
See application file for complete search history.

(56) References Cited

U.S. PATENT DOCUMENTS

| | | | |
|---|---|---|---|
| 4,895,147 A | 1/1990 | Bodicky et al. | |
| 5,279,294 A | 1/1994 | Anderson et al. | |
| 5,487,748 A | 1/1996 | Marshall et al. | |
| 5,971,941 A * | 10/1999 | Simons et al. | 600/573 |
| 6,129,823 A | 10/2000 | Hughes et al. | |
| 6,315,738 B1 | 11/2001 | Nishikawa et al. | |
| 6,377,894 B1 | 4/2002 | Deweese et al. | |
| 6,541,216 B1 | 4/2003 | Wilsey et al. | |
| 6,561,989 B2 | 5/2003 | Whitson | |
| 6,670,115 B1 | 12/2003 | Zhang | |
| 6,783,502 B2 | 8/2004 | Orloff et al. | |
| 6,939,450 B2 | 9/2005 | Karinka et al. | |

(Continued)

FOREIGN PATENT DOCUMENTS

WO 2008039946 A2 4/2008

(Continued)

OTHER PUBLICATIONS

PCT Notification of Transmittal of the International Search Report and the Written Opinion of the International Searching Authority, or the Declaration, in PCT Application No. PCT/US2007/079783, paper dated Apr. 16, 2008, 20 pages.

(Continued)

*Primary Examiner* — Max Hindenburg
*Assistant Examiner* — Adam Eiseman
(74) *Attorney, Agent, or Firm* — Edward J. Bada; Marcus Hunt; Bozicevic, Field & Francis LLP

(57) ABSTRACT

An integrated lancet and testing striplet for measuring a body analyte level in a health care regimen includes a skin piercing member and an analyte sensor coupled together.

18 Claims, 17 Drawing Sheets

U.S. PATENT DOCUMENTS

| | | |
|---|---|---|
| 7,118,667 B2 | 10/2006 | Lee |
| 7,299,081 B2 * | 11/2007 | Mace et al. ............... 600/345 |
| 2002/0002344 A1 | 1/2002 | Douglas et al. |
| 2003/0068666 A1 | 4/2003 | Zweig |
| 2003/0191415 A1 | 10/2003 | Moerman et al. |
| 2003/0209451 A1 | 11/2003 | Dineen et al. |
| 2003/0211619 A1 * | 11/2003 | Olson et al. ................. 436/44 |
| 2003/0212345 A1 * | 11/2003 | McAllister et al. ......... 600/584 |
| 2004/0134779 A1 | 7/2004 | Hsu et al. |
| 2005/0234368 A1 * | 10/2005 | Wong et al. ................. 600/583 |
| 2005/0277850 A1 | 12/2005 | Made et al. |
| 2006/0094985 A1 | 5/2006 | Aceti et al. |
| 2006/0229532 A1 * | 10/2006 | Wong et al. ................. 600/583 |
| 2007/0149897 A1 | 6/2007 | Ghesquiere et al. |
| 2007/0173739 A1 | 7/2007 | Chan |
| 2007/0287191 A1 | 12/2007 | Stiene et al. |
| 2008/0167578 A1 | 7/2008 | Bryer et al. |
| 2009/0321287 A1 | 12/2009 | List et al. |

FOREIGN PATENT DOCUMENTS

| | | |
|---|---|---|
| WO | 2008039949 A2 | 4/2008 |
| WO | 2008039946 A3 | 5/2008 |
| WO | 2008039949 A3 | 6/2008 |

OTHER PUBLICATIONS

PCT Invitation to Pay Additional Fees and Where Applicable Protest Fee, for PCT Application No. PCT/US2007/079783, paper dated Jan. 9, 2008, 2 pages.

* cited by examiner

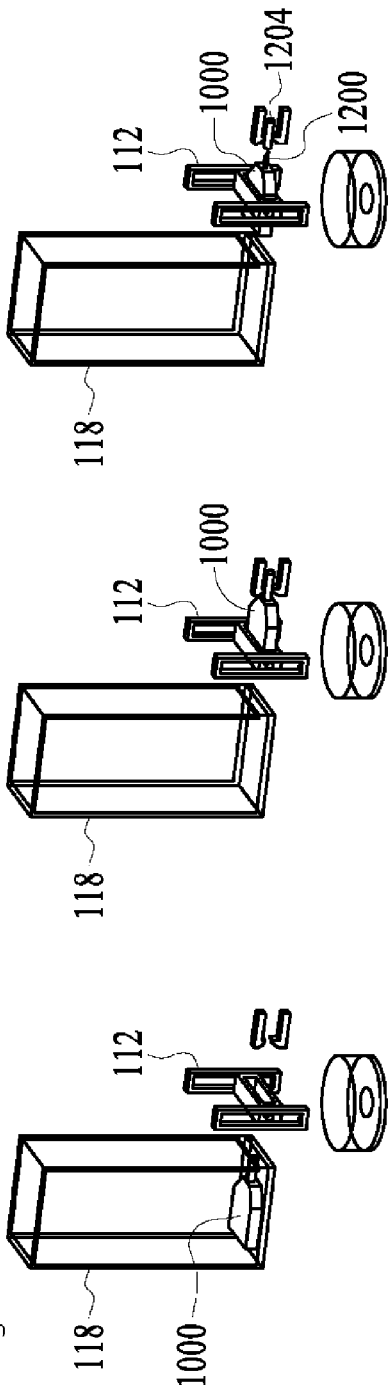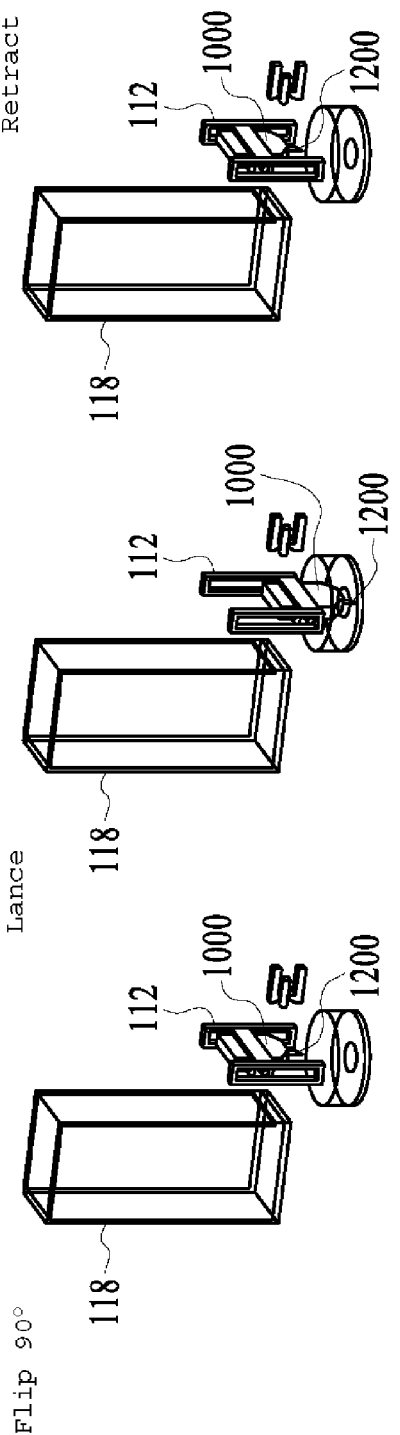

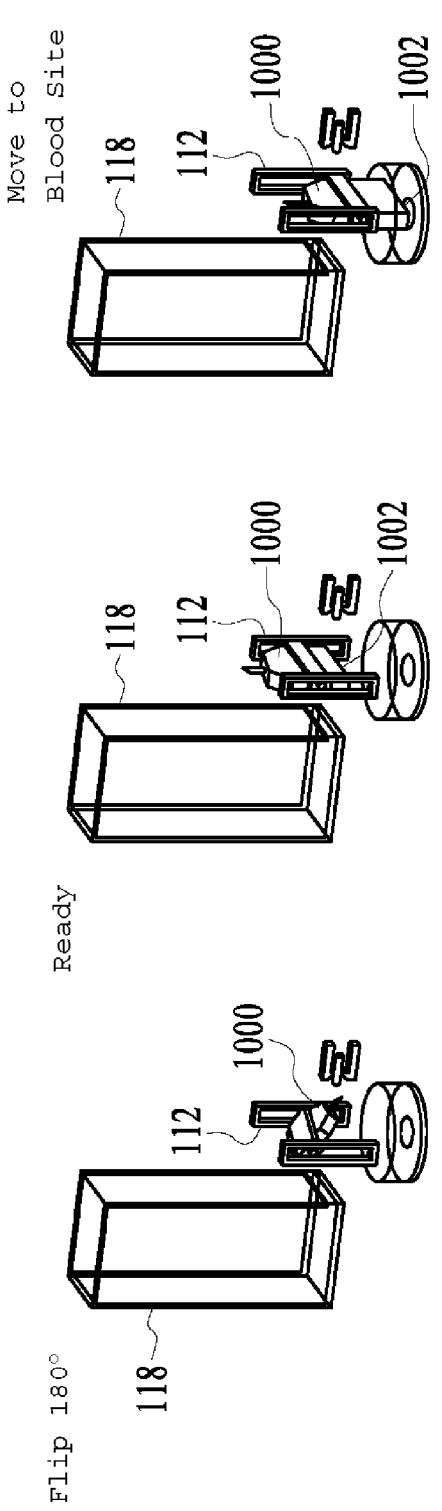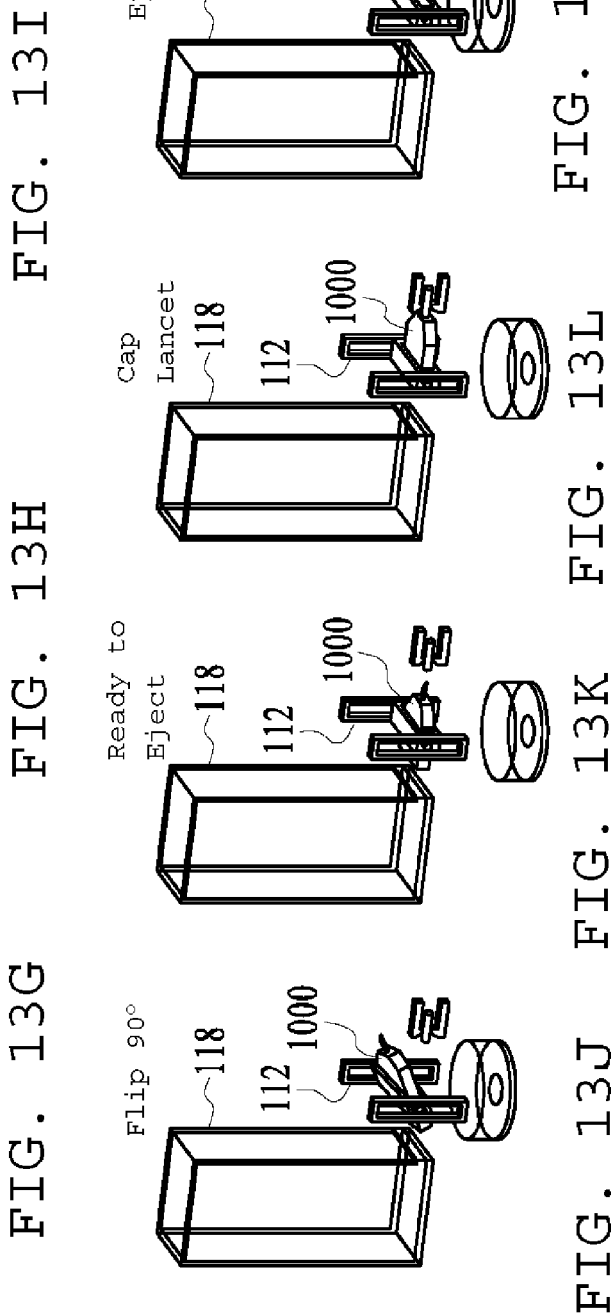

INTEGRATED SENSOR FOR ANALYZING BIOLOGICAL SAMPLES

PRIORITY

This application is a divisional of U.S. patent application Ser. No. 11/535,986, filed on Sep. 28, 2006, which claims the benefit of priority to U.S. provisional patent application No. 60/741,019, filed Nov. 30, 2005. This application is related to PCT application no. PCT/US2007/079783, filed Sep. 27, 2007; and to U.S. patent application Ser. No. 11/535,985, filed Sep. 28, 2006; and PCT application no. PCT/US2007/079778, filed Sep. 27, 2007. Each of these applications is hereby incorporated by reference.

BACKGROUND OF THE INVENTION

1. Field of the Invention

This invention relates to the field of medical diagnostic devices.

2. Discussion of the Related Art

The prevalence of diabetes is increasing markedly in the world. At this time, diagnosed diabetics represent about 3% of the population of the United States. It is believed that the actual number of diabetics in the United States is much higher. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse some of the effects of diabetes.

Glucose monitoring devices known in the art have operated on the principle of taking blood from an individual by a variety of methods, such as by means of a needle or a lancet. The individual then contacts a strip carrying reagents with the blood, and finally inserts the strip into a blood glucose meter for measurement of glucose concentration by optical or electrochemical techniques.

Medical devices of the prior art for monitoring the level of glucose in the blood stream have required that an individual have separately available a needle or a lancet for extracting blood from the individual, test strips carrying reagents for bringing about a chemical reaction with the glucose in the blood stream and generating an optical or electrochemical signal, and a blood glucose meter for reading the results of the reaction, thereby indicating the level of glucose in the blood stream. The level of glucose, when measured by a glucose meter, is read from the strip by an optical or electrochemical meter.

It is desired to simplify the systems, devices, and methods for determining the level of an analyte such as glucose in a body fluid such as blood. In particular, it is desired to integrate the operations of extracting a sample of blood by means of a needle or a lancet, applying the sample of blood to a reagent-bearing test strip, reading the result of a glucose monitoring test, and discarding the used needle or lancet and test strip in a safe and efficient manner.

Certain patents describe devices that can perform steps for determining the concentration of glucose in the blood stream. For example, U.S. Pat. No. 5,632,410 discloses a sensor-dispensing instrument for handling a plurality of fluid sensors (i.e., test strips). However, this patent fails to include a lancing device for puncturing the skin of a patient in order to extract a sample of blood. U.S. Pat. No. 6,908,008 discloses an apparatus that includes a dispenser comprising a housing having a chamber; a means for retaining a plurality of test strips in a substantially moisture-proof, air-tight first position; and a means for opening the chamber and moving one of the plurality of test strips translationally from a first position inside of the chamber to a second position at least partially outside of the chamber, wherein the opening of the chamber and the moving of the one test strip is achieved by a single mechanical motion; and an electrochemical analyzing means for analyzing a biological fluid. However, like, U.S. Pat. No. 5,632,410, this patent fails to simplify the testing process, e.g., this patent fails to include a lancing device for puncturing the skin of a patient in order to extract a sample of blood.

U.S. Pat. No. 5,035,704 discloses a blood sampling mechanism including a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, means for testing the blood sample, means for defining a blood sampling station at which the blood sample is obtained, means for defining a blood testing station at which the blood sample is tested by said blood sample testing means, and means for conveying said test pad from said blood sampling station after the blood sample has been obtained to said blood testing station. The dermis-piercing member and test pad are, however, entirely separate components in this system (see also WO 03/082091). U.S. Pat. No. 5,971,941 discloses a blood sampling apparatus for sampling blood from the skin of a patient for analysis. The apparatus includes a cartridge and a housing with a driver. The cartridge has a cartridge case, lancet, and a compartment associated with the cartridge case for receiving blood. The lancet is housed in the cartridge case and operatively connected thereto such that it is drivable to extend outside the cartridge case through a lancing opening for lancing the skin to yield blood. The housing has a driver for urging the lancet to extend outside the cartridge case. During lancing, the cartridge may be detachably held in the housing such that the cartridge can be disassociated from the driver after sampling blood. The U.S. Pat. No. 5,971,941 discloses that material around a lancet aperture in a cartridge case soaks up blood after lancing (see also U.S. Pat. No. 5,279,294). This does not bring the absorbent material to the center of the sample, and when only a small amount of blood is available such as is often the case in alternate site testing away from fingertips, then testing may be unreliable, may need to be repeated far too often, or may simply require testing at the fingertips. Application of sample fluid to a capillary end leading to reagent material involves careful manual alignment. A manual actuation step is also involves in getting the lancet to protrude from the cartridge.

WO 2004/041082 discloses a device for use with a body fluid sampling device for extracting bodily fluid from an anatomical feature. The device comprises a cartridge having a plurality of cavities. The device may include a plurality of penetrating members each at least partially contained in the cavities of the cartridge wherein the penetrating members are slidably moved to extend outward from openings on the cartridge to penetrate tissue. The device may also include a plurality of analyte detecting members and a plurality of chambers. Each chamber may be associated with one of the cavities, the chambers positioned along an outer periphery of the cartridge, wherein at least one of the analyte detecting members forms a portion of one wall of one of the plurality of chambers.

U.S. Pat. No. 6,352,514 discloses a body fluid sampling device that includes a lancet and a test strip. The lancet is disposed on a lancet carrier, while the test strip is disposed at the end of a capillary tube. Body fluid exposed at a lancing site is drawn up into a capillary tube which is placed into contact with the body fluid. At the end of the capillary tube is a test strip. Once the body fluid is drawn up the capillary tube, it may be applied to the test strip to determine an analyte level. The lancet and the capillary tube and test strip are contained within a same sampling device housing, although they are configured as two separately disposable items and not integrated together as a single item. These items are separately manipulated into, within and out of the housing before, during and after use, respectively.

It would be desirable to develop a test sensor that also serves as a lancet for forming an opening in the skin of a patient to enable a sample of biological liquid to emerge from the patient, so that the sample of bodily fluid may be collected from the patient emerging from the opening in the skin by a test strip, and analyzed to determine a characteristic of the bodily fluid. It would also be desirable to develop a medical diagnostic device that is small in size, reliable to use, and provides accurate results, even when only a small volume of sample of biological liquid is collected.

SUMMARY OF THE INVENTION

Integrated lancet and testing sensors ("striplets") are provided for measuring a body analyte (e.g., glucose) level in a health care (e.g., diabetes) regimen. A lancet body includes a sensor receiving end and a lancet end. A lancet needle is coupled with and protruding from the lancet end. An optional lancet cap may secure the lancet. A sensor is coupled to the test strip receiving end of the lancet body having multiple electrodes and assay chemistry for testing an analyte (e.g., glucose) level of an applied body fluid. In certain embodiments, the test strip and lancet needle are relatively disposed at different ends of the striplet for providing both lancing and application of body fluid at a lancing site by reorienting and advancing the striplet within the meter after lancing to contact a sample receiving portion of the test strip precisely at the lancing site.

In certain embodiments, a striplet includes both a test strip portion and a lancet portion. These may be relatively opposed, e.g., extending about 180 degrees from each other, or extending at another angle from zero to 360 degrees. The lancet portion may couple to the test strip portion as a two-piece device, or each may couple with a lancet body as a three-piece device.

The reorienting may include rotating the striplet when the lancing site remains approximately at the predetermined location relative to the meter for application of body fluid to the sample receiving portion of the test strip. In certain embodiments, the test strip and lancet are symmetrically disposed at opposite ends of the lancet body. The reorienting may include rotating and/or flipping the striplet when the lancing site remains approximately at the predetermined location relative to the meter for application of body fluid to the sample receiving portion of the test strip.

The lancet body may include a pair of relatively disposed recesses for respectively positioning the test strip via a latching mechanism or spring-loaded ball and detent mechanism for lancing and application of body fluid at a same lancing/testing site. The recesses may be trapezoidally-shaped, or another suitable shape.

Embodiments may include a lancet cap. A lancet cap may include one or more elastomeric arms that couple with defined cutouts in the lancet body for snapping the cap into and out of mating relationship with the lancet body by respective application of sufficient coupling and separation force.

The lancet body and test strip may include at least two teeth that fit corresponding slots for coupling the lancet body and test strip together, and the lancet body has the teeth and the test strip has the corresponding slots.

The test strip may include one or more substrates, e.g., may include a first substrate (e.g., a base) and a second substrate (e.g., a cover). The first substrate may have a layer of electrically conductive material applied to one major surface thereof, while the second substrate may have a working electrode (and optionally a trigger electrode) applied to at least one major surface thereof. Electrodes may be coplanar or may be disposed on different surfaces or be opposed. The first substrate may be adhered to the second substrate by a layer of electrically conductive adhesive and/or a layer of non-conductive adhesive.

The sensor-containing portion may include a sample flow channel, and a working electrode and optional trigger electrode may be positioned in the flow channel.

The cover may include at least one electrical passageway running from an inner face to an outer face and/or a slot formed therein to attach the sensor-containing portion to a tab in the lancet-containing body.

The base may include an opening formed therein to attach the sensor-containing portion to a tab in the lancet-containing body.

In certain embodiments, the base or the cover may include a recess formed in an edge thereof that forms the sample receiving portion of the test strip. The recess may have a hydrophilic material applied thereto. The lancet may be positioned approximately 180° from the recess. Electrical contact pads may be on one major surface of the cover and/or base. The cover and/or trigger electrode may include a layer of electrically conductive or semiconductive material, and may include carbon.

Methods of providing a sample of body fluid to a test strip for measuring an analyte level within the fluid are also provided. Embodiments of the subject methods include providing an integrated analyte testing striplet and within a metering chamber, and piercing a lancing site with the lancet needle at a predetermined location relative to the meter. In certain embodiments, the striplet is automatically reoriented and advanced within the meter including contacting with precision a sample receiving portion of the test strip at the lancing site, such that body fluid from the lancing site is applied to the sample receiving portion of the test strip for measuring a level.

The method may also include disarming the lancet needle and disposing of the testing striplet. The lancing site may remain approximately at the predetermined location relative to the meter when body fluid is applied to the sample receiving portion of the test strip. The reorienting may include rotating and/or flipping the striplet. The loading may include mating a first recess defined within the lancet body with a latching mechanism or a ball and detent mechanism of the glucose meter, such that the test striplet is specifically disposed at a lancing orientation. The reorienting may then include mating a second recess defined within the lancet body with the same latching or ball and detent mechanism, such that the testing striplet is specifically disposed at a testing orientation. The recesses may be trapezoidally-shaped, or another suitable shape.

The arming may include uncoupling a lancet cap by uncoupling one or more elastomeric arms of the lancet cap from defined cutouts in the lancet body by application of sufficient separating force. The disarming of the lancet needle may involve snapping the one or more elastomeric arms of the lancet cap back into mating relationship with the defined cutouts of the lancet body by application of sufficient coupling force.

The method may include coupling at least two teeth that fit corresponding slots for coupling the lancet body and test strip together. The lancet body may have the teeth, while the test strip has corresponding slots.

In another embodiment, a test strip includes a lancet-containing portion and a sensor-containing portion. During a time that the test strip is stored in a medical diagnostic device, a protective cover encloses the lancet of the lancet-containing portion. The medical diagnostic device is capable of removing the protective cover to enable the lancet to form an opening in the skin of the patient and is further capable of re-attaching the protective cover onto the lancet to enable the medical diagnostic device to eject the used test strip in a safe manner.

In the case of collection of an inadequate quantity of sample, the medical diagnostic device enables re-lancing. The test sensor may require only a small volume of sample to carry out a complete test such as sub-microliter sample volumes, e.g., 0.5 microliter or less, or 0.3 microliter or less, or 0.2 microliter or less in certain embodiments. The test strip combines a lancet and a sensor in a single small unit. After the skin of the patient is pierced and a sample of biological liquid, e.g., blood, appears, the test strip is moved into position for collecting a sample of the liquid, and the liquid enters the sample application zone of the sensor-containing portion of the test strip without manipulation of the test strip by the user.

An integrated lancing and testing kit is also provided for measuring a body analyte level in a health care regimen. The kit includes a meter for analyzing the analyte to determine the body glucose level, and a cartridge containing one or more integrated lancet and testing striplets. The striplets include features described above and below herein.

BRIEF DESCRIPTION OF THE DRAWINGS

FIGS. 13A-13M are schematic views illustrating positions of a lancing/collecting assembly during one cycle of operation of a medical diagnostic device in accordance with a preferred embodiment.

DETAILED DESCRIPTION

Figure 1:
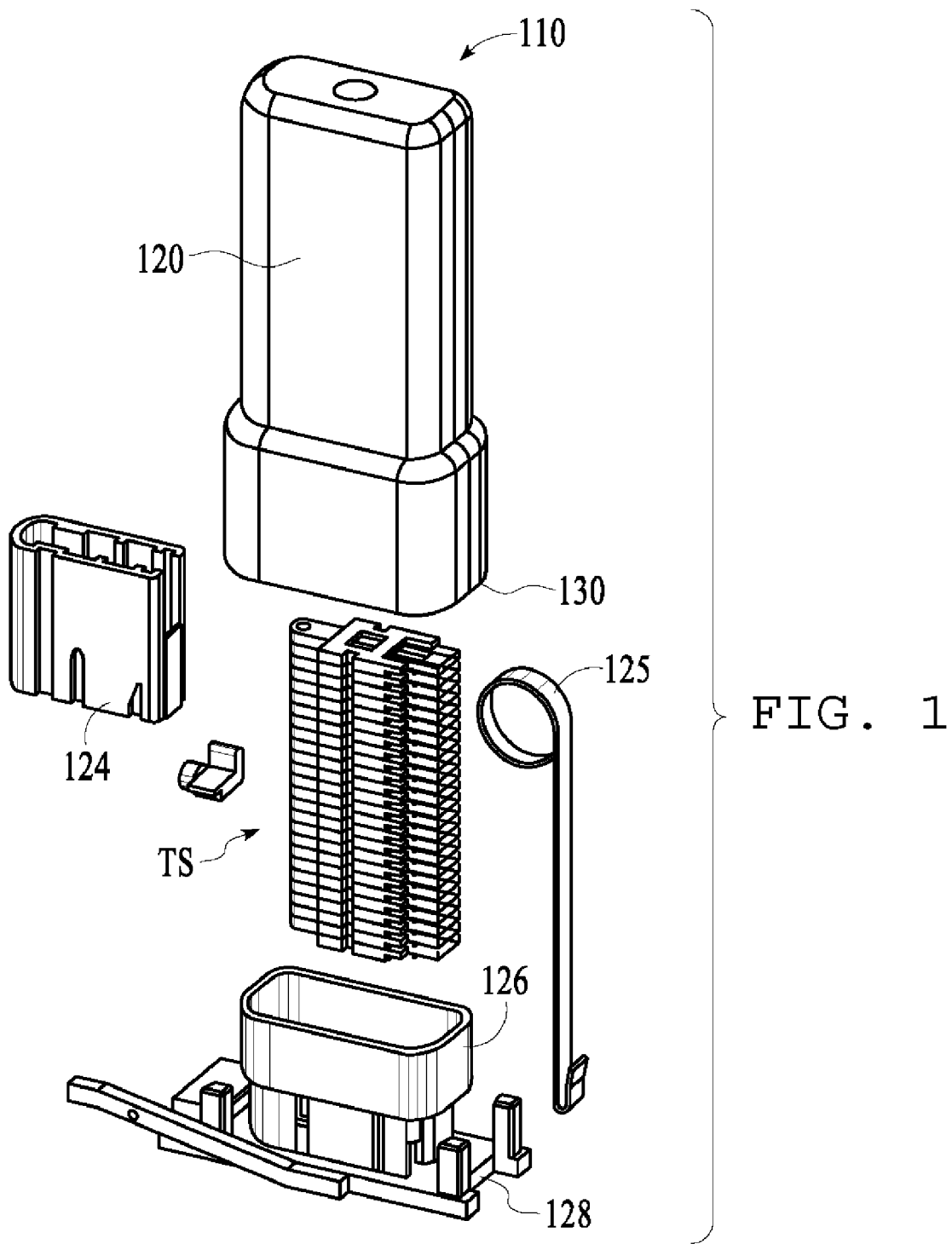
FIG. 1 is an exploded perspective view of an assembly for storing and dispensing test strips in accordance with a preferred embodiment.

As used herein, the expressions "storing/dispensing assembly" and "assembly for storing and dispensing test strips" means a mechanism that is capable of both (a) storing a plurality of test strips in a magazine and (b) advancing the test strips, one at a time, from the magazine to the lancing/collecting assembly. The expression "lancing/collecting assembly" means a mechanism that is capable of both (a) forming an opening in the skin of a patient and (b) collecting a sample of biological liquid emerging from that opening.

In addition, glucose is referred to in many places herein as a representative analyte. However, other analytes include glucose, lactate, and the like, in a body fluid. Additional analytes that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. Any of these analytes may be used and glucose is used throughout as a representative analyte for convenience only and is in no way intended to limit the scope of the invention.

Medical Diagnostic Device

In one embodiment, a medical diagnostic device is provided that carries out the functions of:

(a) storing a plurality of lancets and sensors;
(b) feeding a plurality of lancets and sensors to a system that employs a lancet to form an opening in the skin of a patient and then employs the sensor to collect a sample of biological liquid that emerges from the opening formed in the skin;
(c) forming an opening in the skin of the patient by means of the lancet;
(d) collecting the sample of biological liquid emerging from the opening formed in the skin of the patient by means of the sensor;
(e) analyzing the sample of biological liquid collected by the sensor; and
(f) ejecting the used lancet and the used sensor in a safe manner.

In another embodiment, a lancing/collecting assembly is provided that receives the test strip that includes the lancet-containing portion and the sensor-containing portion. By means of various operations, the lancing/collecting assembly can perform one or more of the following: (a) orient the lancet-containing portion of the test strip in such a manner that the lancet of the lancet-containing portion of the test strip can be advanced toward the skin of the patient in order to form an opening therein, (b) arm the lancet of the lancet-containing portion of the test strip, (c) trigger the armed lancet of the lancet-containing portion of the test strip so that the lancet forms an opening in the skin of the patient, (d) orient the sensor-containing portion of the test strip in such a manner that the sensor-containing portion of the test strip can be advanced toward the opening formed in the skin of the patient to collect a sample of biological liquid emerging from the opening in the skin of the patient, and (e) advance the sensor of the sensor-containing portion of the test strip so that sufficient quantity of the sample of biological liquid can be collected for analysis to determine a parameter of the biological liquid.

The lancing/collecting assembly is also capable of incorporating an analyzer that is capable of analyzing the sample of biological liquid collected from the opening in the skin of the patient.

In another embodiment, a method is provided for using the medical diagnostic device, including:
(a) feeding one of a plurality of test strips, each of the test strips comprising a lancet-containing portion and a sensor-containing portion to a lancing/collecting assembly that employs a lancet of the lancet-containing portion to form an opening in the skin of a patient and then employs a sensor of the sensor-containing portion to collect a sample of biological liquid that emerges from the opening formed in the skin;
(b) forming an opening in the skin of the patient by means of a lancet in the lancet-containing portion;
(c) collecting a sample of biological liquid emerging from the opening formed in the skin of the patient by means of the sensor of the sensor-containing portion;
(d) analyzing the sample of biological liquid collected by the sensor of the sensor-containing portion; and
(e) ejecting the used test strip in a safe manner.

As illustrated at FIG. 1, an assembly for storing and dispensing test strips 110 includes a magazine for storing multiple test strips "TS", each test strip including a lancet-containing portion and a sensor-containing portion. Test strips that are suitable for use with the medical diagnostic device of this invention are illustrated in FIGS. 4-11, inclusive, and described in detail in the text accompanying those figures. The assembly 110 includes an exterior cover 120. The purpose of the exterior cover 120 is to maintain the test strips in a substantially moisture-tight, air-tight condition. A variety of materials are suitable for forming the exterior cover 120 and include rubber and other polymeric materials, and the like. A platform 124 is for containing a biasing element 125, e.g., a constant force spring, for urging test strips toward the location in the magazine 118 from which test strips are fed to the lancing/collecting assembly. An insert 126 is for securing the biasing element 125. The platform 124 may be filled with a desiccant, in order to enhance moisture resistance of the test strips stored within the assembly 110. Below the magazine 118 is a test strip track 128 for providing a guide path for a test strip when the test strip is being fed to the lancing/collecting assembly. The test strip track 128 also abuts against a seal 130 attached to the bottom end of the assembly 110. The seal 130 surrounds the bottom end of the magazine 118 and is typically made from a substantially air-impermeable, moisture-impermeable material, such as, for example, rubber or a polymeric material, or the like. The combination of the test strip track 128 and the seal 130 provides a substantially moisture-tight, air-tight seal for the assembly 110.

Figure 2:
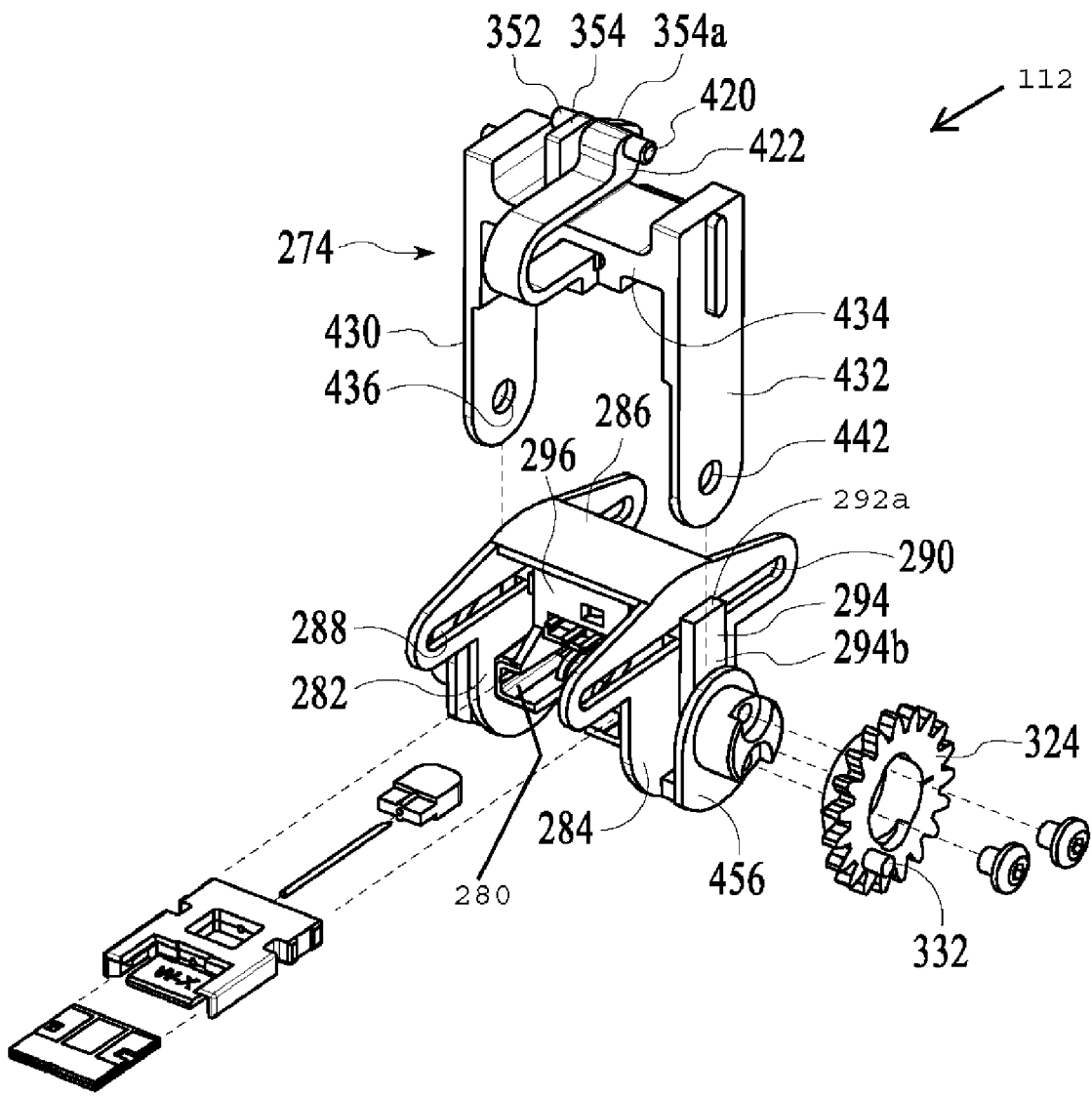
FIG. 2 is an exploded perspective view of selected components of the lancing/collecting assembly of a medical diagnostic device including an integrated lancet and testing striplet in accordance with a preferred embodiment.
Figure 3:
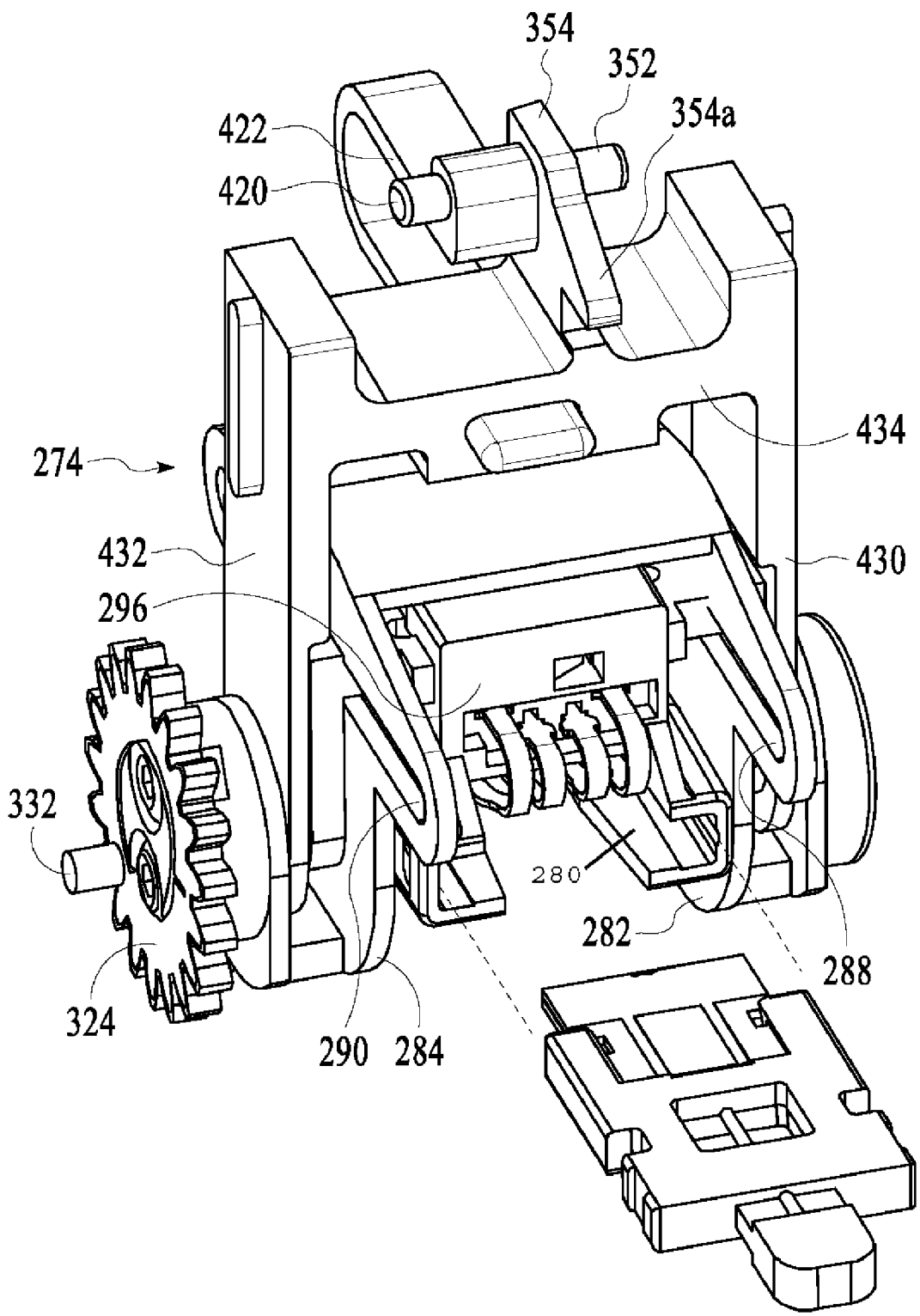
FIG. 3 is another perspective view of selected components of the lancing/collecting assembly of a medical diagnostic device illustrating entry of an integrated lancet (with cover) and testing striplet in accordance with a preferred embodiment.

Referring now to FIGS. 2 and 3, a first embodiment of a lancing/collecting assembly 112 includes a cradle 280. The cradle 280 holds a test strip during both the lancing step and the sample collecting step, which are carried out by the medical diagnostic device. The cradle 280 also orients a test strip for lancing, and reorients the test strip for sample collecting, so that the lancet of the lancet-containing portion of the test strip can form an opening in the skin of the patient during lancing and the sensor of the sensor-containing portion of the test strip can collect the sample of biological liquid emerging from the opening in the skin of the patient during sample collecting, e.g., without manual intervention. In the embodiment shown in FIGS. 2 and 3, the cradle 280 also holds the test strip during analyzing. The cradle 280 includes two upright members 282 and 284 and a transverse member 286. The transverse member 286 of the cradle 280 connects the two upright members 282 and 284 of the cradle 280. The upright member 282 of the cradle 280 has a slot 288 formed therein, and the upright member 284 of the cradle 280 has a slot 290 formed therein. The slots 288 and 290 receive an L-shaped element 292 and 294, respectively, formed on a carrier 296. The L-shaped element 294 has a foot 294*a* and a leg 294*b*. The L-shaped element 292 also has a foot and a leg which are not shown. The foot 294*a* of the L-shaped element 294 is capable of sliding in the slot 290 (and correspondingly for element 292 and slot 288) of the cradle 280 during lancing and sample collecting, so that the lancet of the lancet-containing portion of the test strip can form an opening in the skin of the patient during lancing and the sensor of the sensor-containing portion of the test strip can collect the sample of biological liquid emerging from the opening in the skin of the patient during collecting. The sliding motion of the foot 294*a* is brought about by the movement of a cam follower 274 during lancing and during sample collecting.

The carrier 296 houses the electrical components and electronic components for completing a circuit when the test strip has received a sample of biological liquid from the patient. FIGS. 2 and 3 illustrate how the carrier 296 receives and holds a test strip. Examples of electrical and electronic components of the carrier 296, and types of analyses that can be performed by the carrier 296 are described in detail in U.S. Pat. Nos. 6,299,757 and 6,616,819.

Referring now to FIGS. 2 and 3, the lancing/collecting assembly 112 includes a transmission system, and may include multiple gears for performing one or more of: (1) enabling operation of components required for a lancing operation for forming an opening in the skin of a patient, (2)

collecting the sample of biological liquid emerging from the opening in the skin of the patient formed by the lancing operation, and (3) positioning a test strip during the analyzing operation. Other configurations of gears, racks, can be used in place of the configuration shown in FIGS. 2 and 3. Transmission systems that utilize components other than gears may be used. The transmission system of the lancing/collecting assembly includes gears shown in FIGS. 2 and 3, and may be replaced in whole or in part by subsystems involving one or more racks and one or more pinions. In certain embodiments, cam follower 274 can be effected in two directions, the directions being separated by approximately 180°, and the cradle 280 or equivalent can be capable of being rotated approximately 180° from a first position to a second position, the first position and the second position being separated by approximately 180°. As used herein, the expression "approximately 180°" means an angle ranging from about 160° to 200°, with angles being close to 180° in many embodiments. In alternative embodiments, the directions may be any angle depending on the configuration of the medical diagnostic device and the relative locations of the lancet and testing strip portions of the integrated lancing and testing striplet. For example, the lancet needle and testing striplet could protrude from a lancet body at other than about 180 degrees from each other, e.g., about 90 degrees or about zero degrees.

Devices for mechanical transmission of power, or "mechanisms", constitute the basic units from which all kinds of devices are built. Every mechanism includes individual elements whose movements in relation to one another are "positive", i.e., the motion of one element produces an accurately determinable and definable motion of every individual point of the other elements of that mechanism. Numerous combinations and modifications are possible, and a few illustrative types of mechanisms are noted here:

(1) Screw mechanism: When a screw spindle is rotated, the element attached to the nut will move in the longitudinal direction of the screw. Conversely, if the nut is rotatably mounted in the frame of the mechanism and driven, the screw spindle will move longitudinally.

(2) Linkage or crank mechanism: The characteristic element is the crank, which is rotatably mounted on a frame and is usually so designed that it can perform complete revolutions. Its motion is transmitted through the coupler (or connecting rod) to the lever (or rocker arm), likewise rotatably mounted, but not performing complete revolutions. Alternatively, instead of being connected to a lever, the coupler may be attached to a sliding element—e.g., a piston.

(3) Pulley mechanism: Connection between pulleys on their respective shafts is effected by flexible elements (belts, ropes).

(4) Ratchet mechanism: This serves to arrest a motion or to produce an intermittent rotation in the driven element. The pawl allows the ratchet wheel to rotate in one direction only, preventing rotation in the opposite direction by engaging the specially shaped teeth on the wheel.

(5) Gear mechanism: This type of mechanism, which is used extensively herein, transmits rotary motion from one shaft to another, usually in conjunction with a change in rotational speed and torque. In a gear mechanism of the usual type, the transmission is effected by the meshing of gear teeth, but in a friction-gear mechanism, this positive drive is replaced by frictional contact of wheels or rollers.

(6) Cam mechanism: This type of mechanism, which is used extensively herein, involves a cam mounted on a frame. The cam is driven and thereby moves a follower, which performs a desired predetermined motion depending on the shape of the cam.

Further information relating to the foregoing mechanisms can be found in "The Way Things Work", Volume 2, Simon and Schuster (New York: 1971), pages 198-217, incorporated herein by reference.

With respect to the interaction between the cradle 280, the carrier 296, the L-shaped elements 292 and 294, the lancet-containing portion of the test strip, and the sensor-containing portion of the test strip, the lancet of the lancet-containing portion of the test strip is moved toward the skin of the patient to form an opening in the skin of the patient. After an opening is formed in the skin of the patient during the lancing step, and after the lancet-containing portion of the test strip is retracted, the test strip is oriented so that the sensor-containing portion of the test strip can collect a sample of biological liquid, e.g., blood, emerging from the opening in the skin of the patient.

In certain embodiments of the lancing/collecting assembly, the mechanical transmission system orients the test strip by rotating the cradle 280 approximately 180° (when the sensor and lancet protrude approximately 180° from the lancet body, see FIG. 4), so that the sensor-containing portion of the test strip faces the opening in the skin of the patient. Unlike lancing, no arming or triggering is involved. However, the test strip moves in the same manner as it did during the lancing, even though it is reoriented for testing instead of lancing, thereby enabling the sensor of the sensor-containing portion of the test strip to contact the sample of biological liquid emerging from the opening in the skin of the patient. The sensor of the sensor-containing portion of the test strip receives a sufficient quantity of the sample to carry out a determination of the analyte. In an embodiment of a lancing/collecting assembly, the carrier 296 may be designed to carry out the determination of the analyte. During the assay or after the completion of the assay, the cradle 280 may be rotated, e.g., about 90°, by the mechanical transmission system to position the test strip for re-attaching the protective cover to the used lancet of the lancet-containing portion of the test strip, removing the used test strip from the lancing/collecting assembly, and disposing of the used test strip through an ejection port in a housing (not shown).

The medical diagnostic device can include a mechanism for ejecting used test strips from the cradle 280. This mechanism may be operated by employing a user-actuated pushing assembly or a motor-actuated pushing assembly to push a used test strip out of the cradle 280 and out of the ejection port of the housing.

To operate the lancing/collecting assembly, a motor can be used to apply a rotating drive input. Alternatively, any rotating drive source could be used, e.g., manual input by the user.

Further detailed description of the medical diagnostic device is found at contemporaneously filed application which is assigned to the same assignee, and at the priority provisional application identified herein above.

Test Strips

Figure 4A:
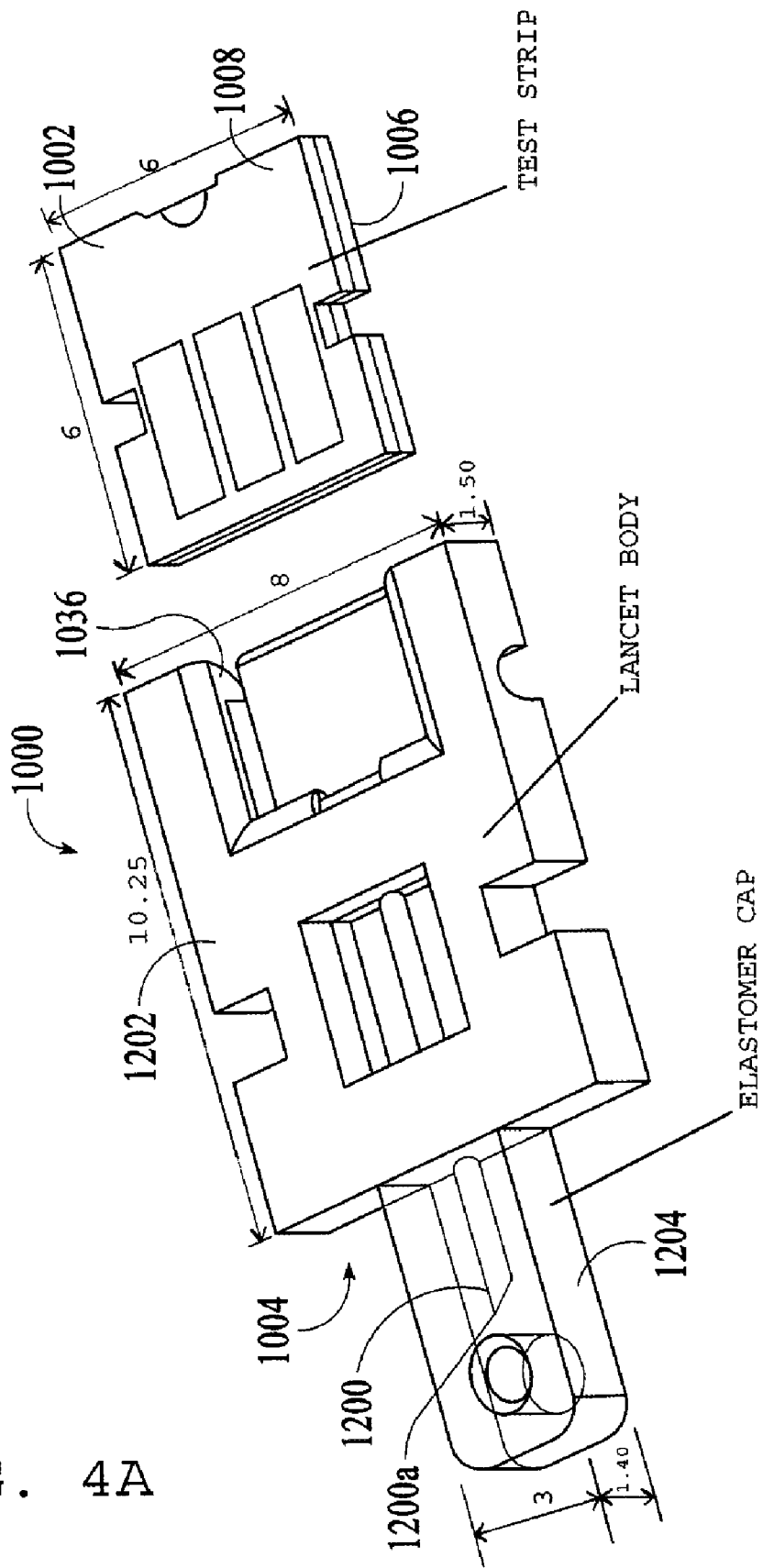
FIG. 4A is a partially-exploded, perspective view of one embodiment of an integrated lancet and testing striplet, showing a lancet bearing a removable protective cover.
Figure 4B:
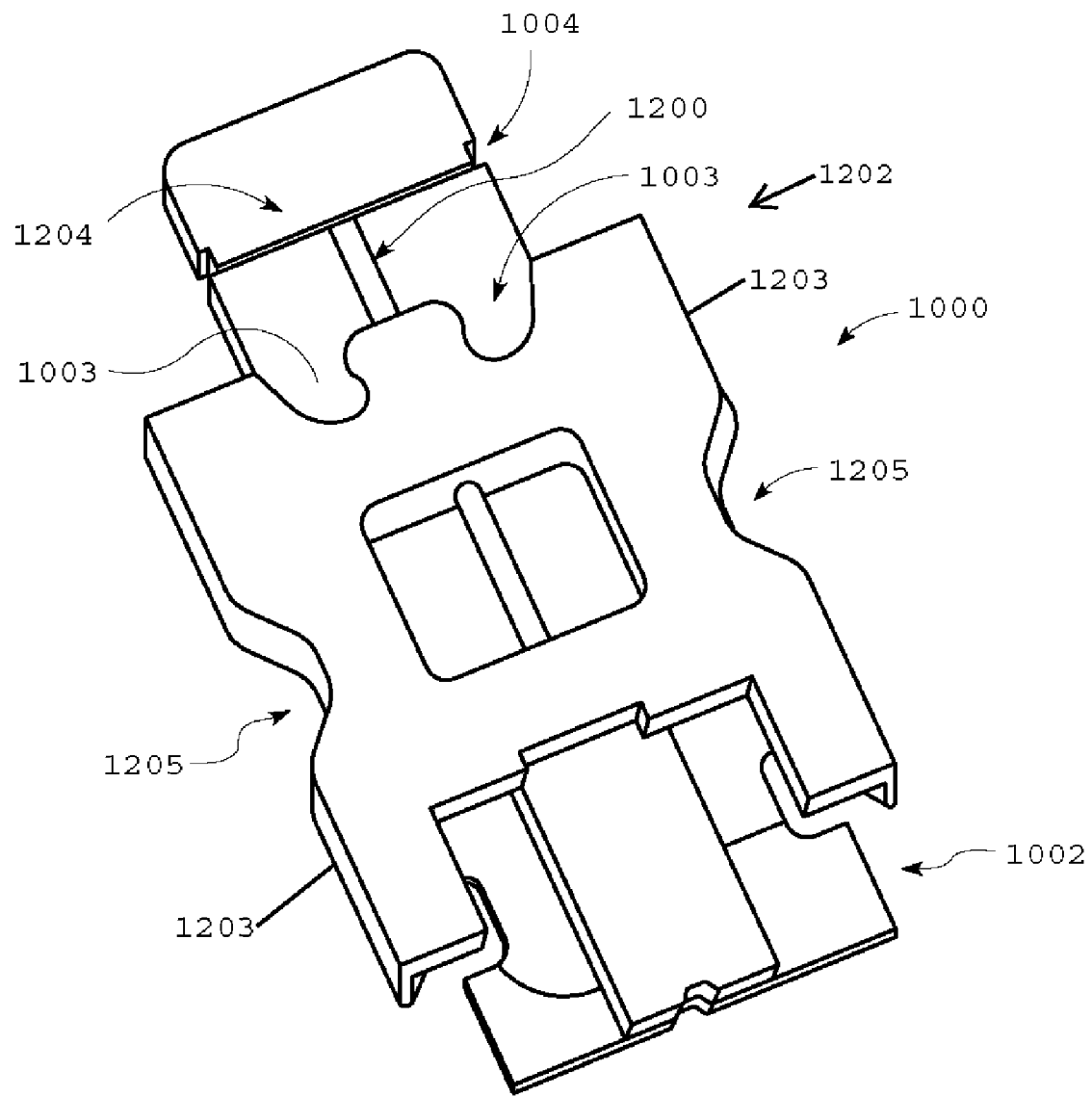
FIG. 4B illustrates another embodiment of an integrated lancet and testing striplet.
Figure 5:
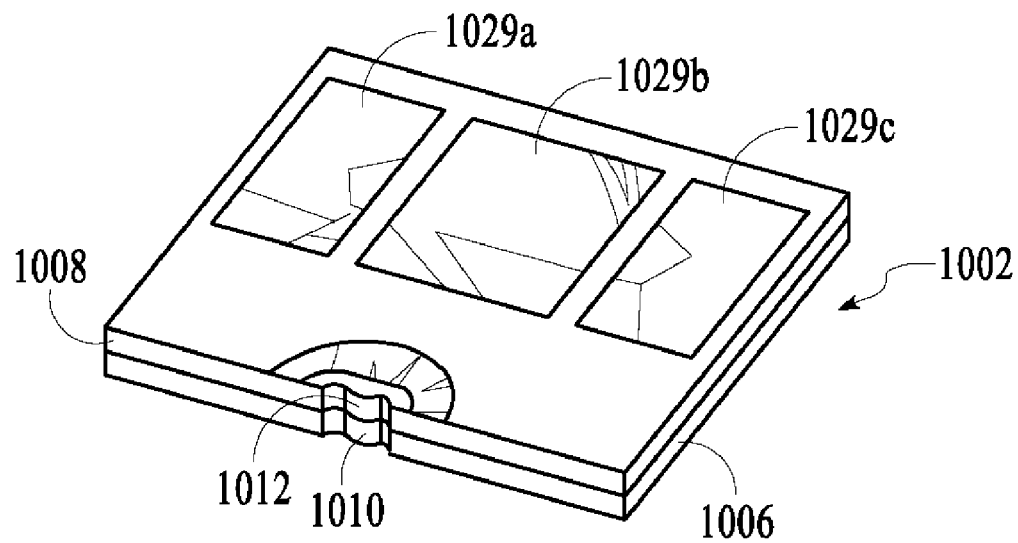
FIG. 5 is a perspective view of the sensor-containing portion of the embodiment of the test strip shown in FIG. 4.

As noted above, novel sensors ("striplets") are provided. The striplets may be used with the medical diagnostic devices described herein, or other suitable devices. An embodiment of a striplet is shown in FIG. 4A, which shows test striplet 1000 has a sensor-containing portion 1002 and a lancet-containing portion 1004. In one embodiment, the sensor-containing portion 1002 includes a first substrate 1006 (a base) and a second substrate 1008 (a cover). FIG. 4B illustrates another embodiment of an integrated lancet and testing striplet 1000, including a sensor-containing portion 1002 and a lancet-containing portion 1004 each coupled to a lancet body 1202. The lancet containing portion includes a lancet 1200 shown protected by an optional elastomer cover 1204 in FIG. 4B. The elastomer cover 1204 includes a pair of arms 1003 that are configured to fit with corresponding cut-outs in the lancet body 1202, so that the cover 1204 can be slipped on and off by application of sufficient coupling and separating force, respectively.

The lancet body includes sides 1203 that are symmetric and may be substantially identical. Each side 1203 is mostly flat like the walls of a tray of carrier 280 (see FIGS. 2 and 3), yet include a recess 1205 that is suitably shaped, e.g., trapezoidally-shaped, or the like. The recesses 1205 are for coupling with a mating mechanism, e.g., a latching mechanism or a ball and detent mechanism that may be spring-loaded, or the like. When the position of one of the recesses 1205 is matched with the mating mechanism, e.g., the latch or the ball of the ball and detent mechanism, a force is provided for maintaining the striplet 1000 specifically in a certain position relative to the analyte meter or other diagnostic medical device, either when lancing or when receiving body fluid at the sensor 1002. That is, the latch or ball and detent mechanism, or the like, holds the striplet in place for lancing by fitting into one of the recesses 1205, and then when the striplet is appropriately moved, e.g. rotated and/or flipped, so that the sensor can receive body fluid at the lancing site, the latch or ball and detent mechanism then holds the striplet in place by fitting into the other one of the recesses 1205, while the latch or the ball and detent mechanism need not itself move other than the ball sliding along the walls 1203 and moving into and out of each slot 1205. In many embodiments, only the striplet is moved between lancing and testing, such that the meter and the lancing site relative to the meter may remain stationary while the striplet is reoriented, e.g., by rotation and/or by being flipped.

Figure 6A:
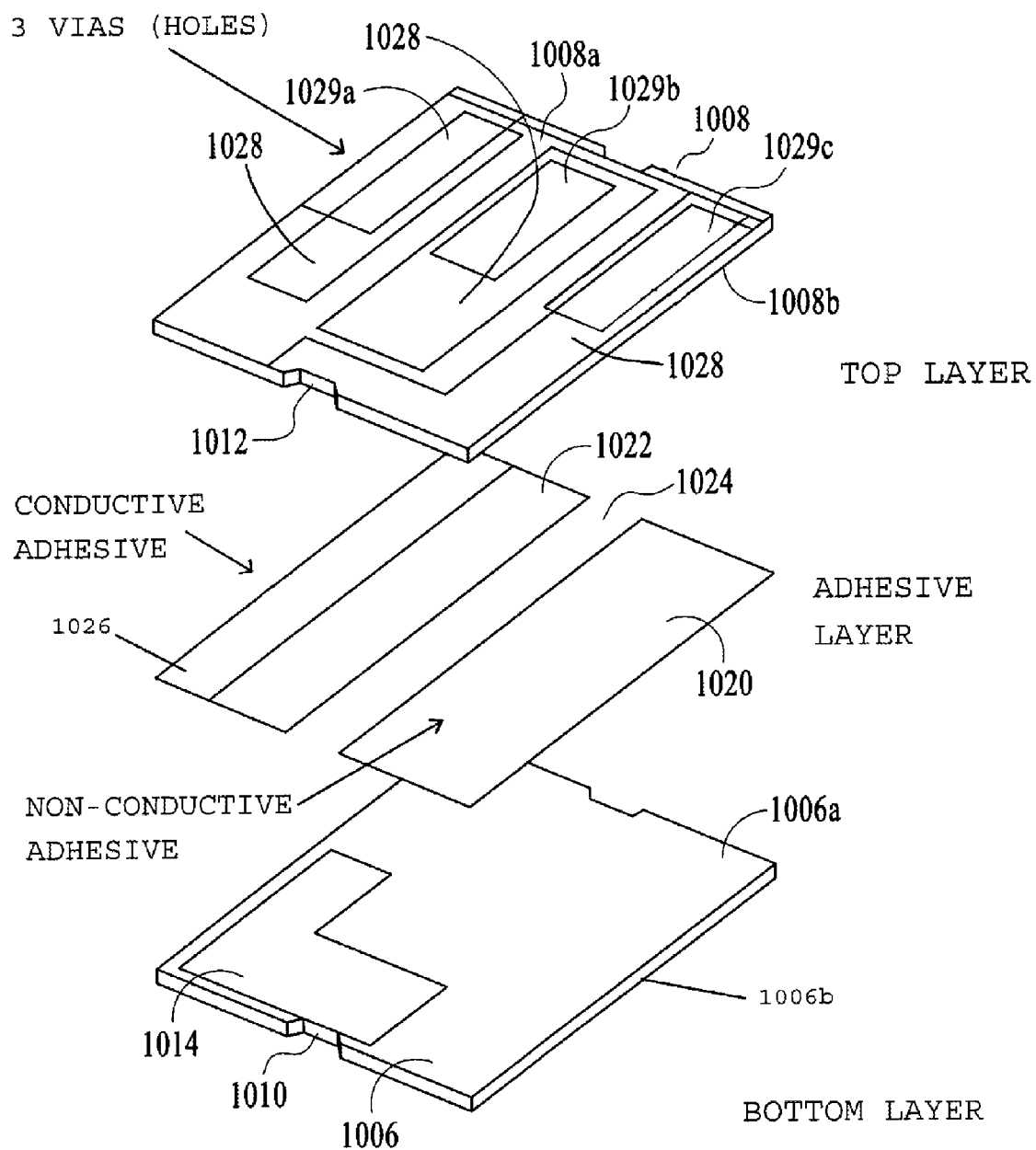
FIG. 6A is an exploded perspective view of the sensor-containing portion of the test strip shown in FIG. 5. In this view, the recesses for tabs of the lancet-containing portion of the test strip are not shown.
Figure 6B:
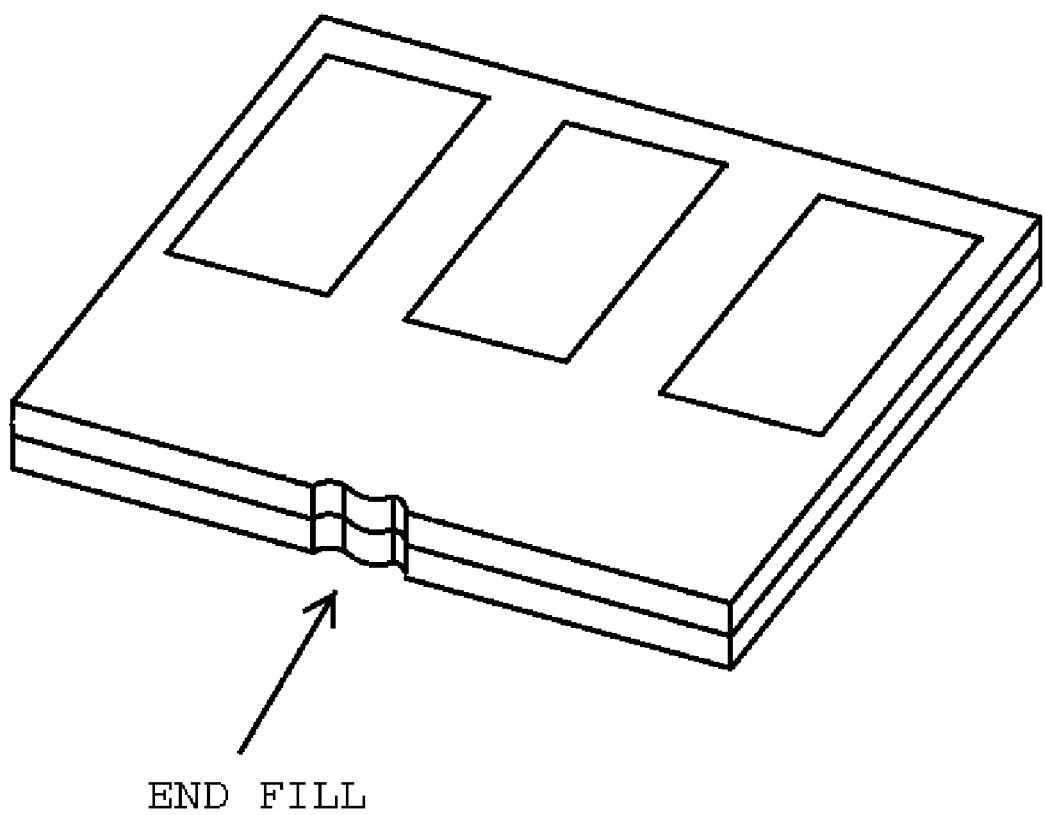
FIG. 6B illustrates the sensor-containing portion of FIG. 6A including an end fill strip with a hydrophilic end fill recess in accordance with a preferred embodiment.

As shown in FIGS. 4A-7B, inclusive, and particularly at FIG. 6A, both the base 1006 and the cover 1008 are substantially rectangular in shape, although other shapes may be used The base 1006 has two major surfaces 1006a, 1006b and in this substantially rectangular embodiment four edges 1006c, 1006d, 1006e, and 1006f. The cover 1008 has two major surfaces 1008a, 1008b and in this substantially rectangular embodiment four edges 1008c, 1008d, 1008e, and 1008f. The base 1006 may include a recess 1010 formed in one edge thereof, and the cover 1008 has a recess 1012 formed in one edge thereof. The surfaces of these recesses 1010 and 1012 may bear a hydrophilic material in order to enable the sample of biological liquid to have greater affinity for the recesses 1010 and 1012 than if the recesses were not bearing a hydrophilic material. The base 1006 and the cover 1008 may be made from an electrically non-conducting material, e.g., an insulating material, that is not capable of carrying substantial electric charge or current. Examples of materials usable include polyesters, polyethylene (both high density and low density), polyethylene terephthalate, polycarbonate, vinyls, and the like. The material may be treated with a primer or other such coating to improve the adhesion of the electrodes thereon. In certain embodiments, the base and/or cover is made from a hydrophobic polymeric material, e.g., "MELINEX" polymer, or the like.

FIG. 6A further illustrates a base 1006 that bears a layer of electrically conductive material 1014 on the major surface thereof facing the cover 1008. Conductive material that may be used include gold, carbon, platinum, ruthenium dioxide, palladium, and conductive epoxies, such as, for example, ECCOCOAT CT5079-3 Carbon-Filled Conductive Epoxy Coating (available from W. R. Grace Company, Woburn, Mass.), Ag/AgCl, Ag/AgBr, as well as other materials known to those skilled in the art. For example, the embodiment of FIG. 6A may include Ag/AgCl. For example, this electrically conductive material may function as a counter electrode or as a dual-purpose reference/counter electrode. The major surface of the cover 1008 facing the base 1006 bears a layer of electrically conductive material 1016 in a first area, which layer of electrically conductive material. Any suitable conductive material may be used, such as described above. For example, the conductive material may constitute a working electrode. In certain embodiments, a layer of electrically conductive material 1018 may be present in a second area, which layer of electrically conductive material may constitute a trigger electrode. The major surface of the cover 1008 facing the base 1006 also bears a layer of non-conductive adhesive 1020 in a first area and layer of non-conductive adhesive 1022 in a second area to bond the cover 1008 to the base 1006.

The layers of non-conductive adhesive 1020, 1022 also function to space the cover 1008 from the base 1006 so that a channel 1024 running along the center of the sensor-containing portion 1002 of the test strip 1000 is formed. A layer of electrically conductive adhesive 1026 enables the transfer of signal from the major surface 1006a of the base 1006 to the major surface 1008b of the cover 1008. The layer of electrically conductive adhesive 1026 may be made from a pressure-sensitive adhesive doped with an electrically conductive material, e.g., carbon. The layer of electrically conductive adhesive 1026 may be any suitable thickness, and in certain embodiments, it has a thickness of about 0.002 inch.

At least one electrical passageway 1028 enables the transfer of signal from the major surface 1008b of the cover 1008 to the major surface 1008a of the cover 1008. An electrical passageway is a passageway formed in the cover 1008. The at least one electrical passageway 1028 is filled with electrically conductive material, such as, for example, any described herein. In certain embodiments the passageway includes carbon. The benefit resulting from the use of one or more electrical passageways is that all of the contact pads 1029a, 1029b, 1029c of the sensor-containing portion 1002 of the test strip 1000 can be positioned on one major surface of the cover 1008 of the test strip 1000.

Figure 7A:
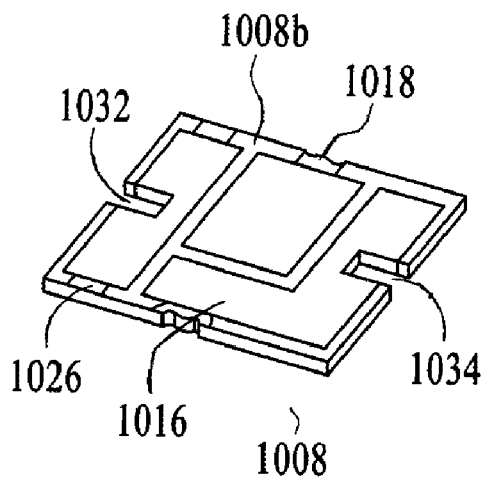
FIG. 7A is a perspective view of the inner face of the cover of the sensor-containing portion of the test strip shown in FIG. 4. In this embodiment, recesses for tabs of the lancet-containing portion of the test strip are illustrated.
Figure 7B:
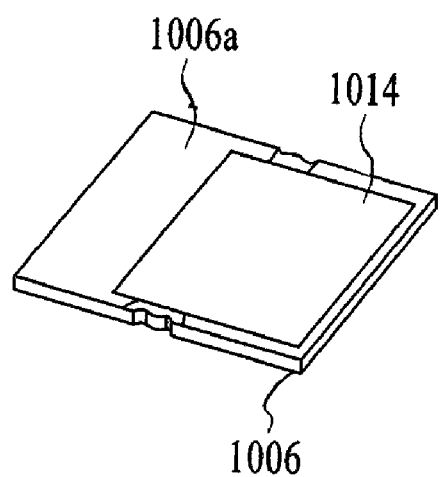
FIG. 7B is a perspective view of the inner face of the base of the sensor-containing portion of the test strip shown in FIG. 4.
Figure 7C:
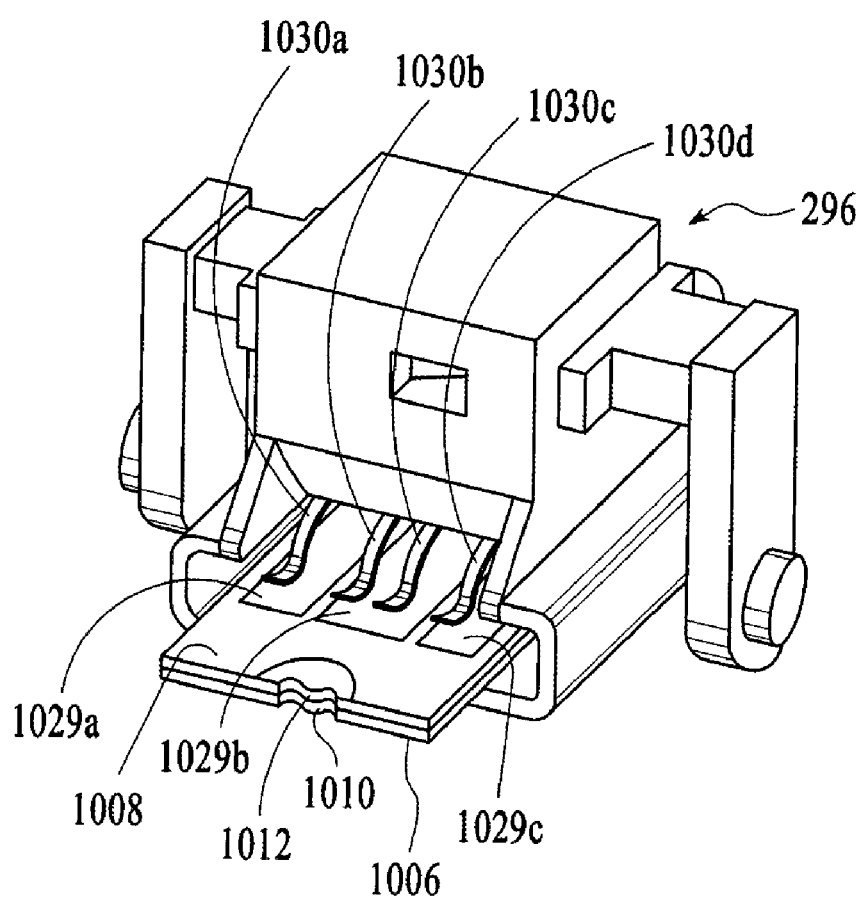
FIG. 7C is a perspective view of the test strip of FIG. 4 inserted into an analyzer of a medical diagnostic device in accordance with a preferred embodiment.

In many embodiments, the dimensions of the sensor-containing portion 1002 of the test strip 1000 are as small as possible in order to reduce the size of the magazine 118 and reduce the volume of sample required to carry out a test. For example, dimensions of the base 1006 and cover 1008 may be approximately 6 mm×6 mm×<2 mm, although other dimensions may be used. Dimensions of the electrodes and dimensions of a sample flow channel 1024 that may be used are described in U.S. Pat. Nos. 6,299,757 and 6,616,819. When the sample of biological liquid is introduced at the sample receiving end, e.g., at hydrophilic recesses 1010, 1012, if present, the liquid is easily drawn up into the channel 1024, along which the liquid flows by means of capillary attraction. The major surface 1008a of the cover 1008 not facing the base 1006 has electrical contact pads 1029a, 1029b, 1029c exposed, which electrical contact pads 1029a, 1029b, 1029c are in contact with the contact leads 1030a, 1030b, 1030c, 1030d of the carrier 296, as shown in FIG. 7C.

The cover 1008 also has two recesses 1032, 1034 in the edges perpendicular to the edge having the sample uptake recess 1012. The function of these recesses 1032, 1034 in the sides is to securely attach the sensor-containing portion 1002 of the test strip 1000 to the lancet-containing portion 1004 of the test strip 1000, which holds the lancet in place. As shown in FIG. 4, the tabs 1036 and 1038 project downwardly from the lancet-containing portion 1004 of the test strip 1000 toward the recesses 1032, 1034 in the edges of the sensor-containing portion 1002 of the test strip 1000. In certain embodiments, the lancet and strip do not physically contact each other.

As noted above, the striplets may be used with a meter or other electrical device having an electrical connector, which is configured to couple with and contact the contact pads at the end of a sensor, such as described above. A meter for use with the striplets typically includes a potentiostat or other component to provide a potential and/or current for the electrodes of the sensor. The meter also typically includes a processor (e.g., a microprocessor or hardware) for determining the concentration of an analyte from the signals from the sensor.

The meter may also include a visual display or port for coupling a display to the sensor and /or audio componentry. The display displays the signals from the sensor and/or results determined for the signals from the sensor including, for example, the concentration of an analyte, and/or the exceeding of a threshold of the concentration of an analyte (including, for example, hypo- or hyperglycemia). Furthermore, the meter may be configured to indicate to the user, via, for example, an audible, visual, or other sensory-stimulating alarm, when the level of the analyte is at or near a threshold level. For example, an alarm system may be included. For example, if glucose is monitored then an alarm may be used to alert the user to a hypoglycemic or hyperglycemic glucose level and/or to impending hypoglycemia or hyperglycemia.

The electrical connector employs contact leads that provide electrical connection between the sensor and the meter. The leads have proximal ends to physically contact the contact pads and distal ends to connect to any attached meter. The end of the sensor that has the contact pads can be slid into or mated with the electrical connector by placing the sensor into a slide area, which provides a support for and retains the sensor. It is important that the contact leads of the electrical connector make electrical contact with the correct pads of the sensor so that the working electrode and counter electrode(s) are correctly coupled to the meter. In certain embodiments of the medical diagnostic device 100 described herein, the carrier 296 substantially performs the aforementioned functions of the meter that is described in U.S. Pat. No. 6,616,819.

Figure 8A:
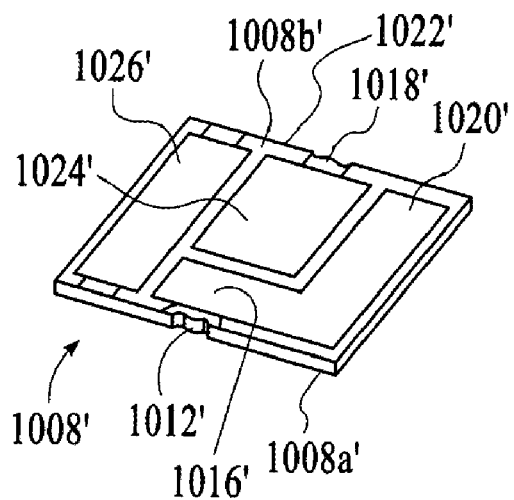
FIG. 8A is a perspective view of the inner face of the cover of another embodiment of the sensor-containing portion of the test strip.
Figure 8B:
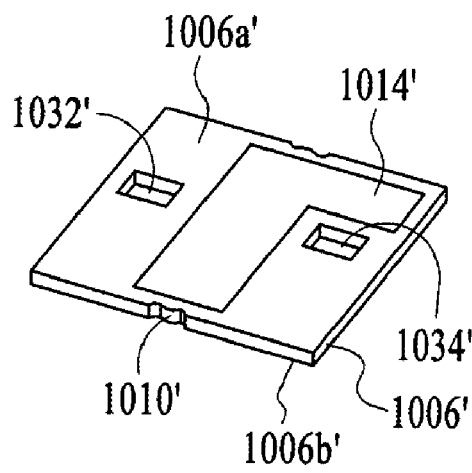
FIG. 8B is a perspective view of the inner face of the base of the sensor-containing portion of the test strip illustrated in FIG. 8A. In this embodiment, the openings for tabs of the lancet-containing portion of the test strip are shown.
Figure 8C:
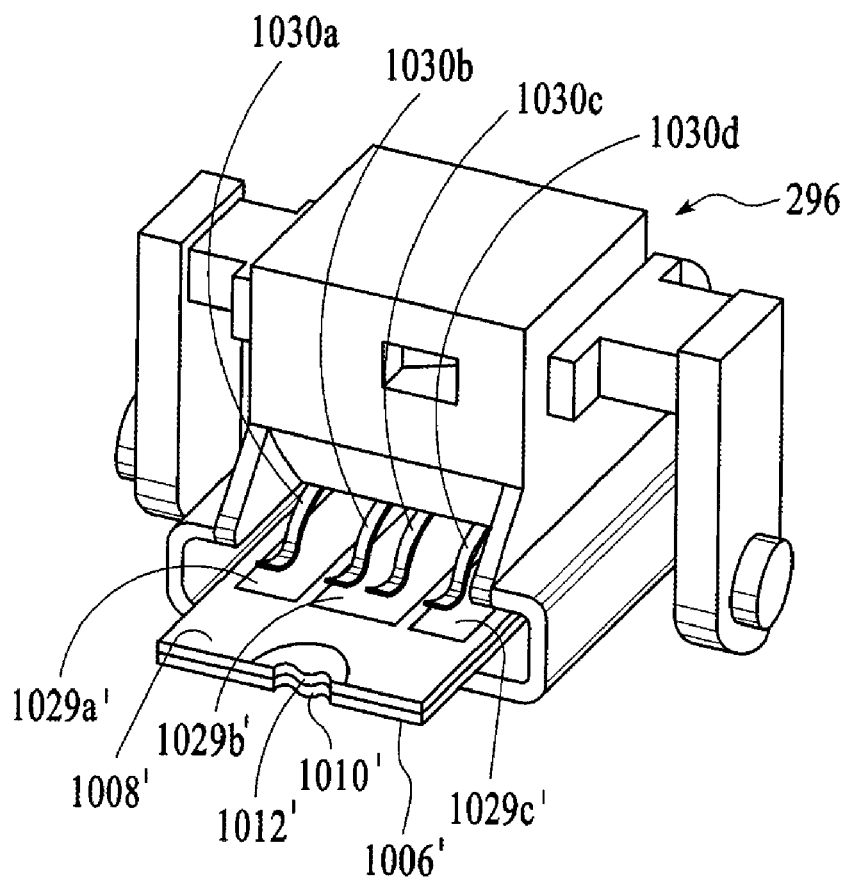
FIG. 8C is a perspective view of the test strip made from the base shown in FIG. 8A and the cover shown in FIG. 8B inserted into an analyzer of a medical diagnostic device in accordance with a preferred embodiment.

In another embodiment, the sensor-containing portion 1002' includes a base 1006' and a cover 1008'. As shown in FIGS. 8A-8C, inclusive, both the base 1006' and the cover 1008' are substantially rectangular in shape, but other shapes may be employed. The base 1006' has two major surfaces 1006a', 1006b' and in this substantially rectangular embodiment four edges 1006c', 1006d', 1006e', and 1006f'. The cover 1008' has two major surfaces 1008a', 1008b' and in this substantially rectangular embodiment four edges 1008c', 1008d', 1008e', and 1008f'. The base 1006' has optional recess 1010' formed in one edge thereof, and the cover 1008' has a recess 1012' formed in one edge thereof. The surfaces of these recesses 1010' and 1012' may bear a hydrophilic material in order to enable the sample of biological liquid to have greater affinity for the recesses 1010', 1012' than if the recesses were not bearing a hydrophilic material.

The base 1006' bears a layer of electrically conductive material 1014' (for example, Ag/AgCl) on the major surface thereof facing the cover layer 1008'. This electrically conductive material functions as a dual purpose reference/counter electrode. The major surface of the cover 1008' facing the base 1006' bears a layer of electrically conductive material 1016' in a first area, which layer of electrically conductive material constitutes a working electrode, and a layer of electrically conductive material 1018' in a second area, which layer of electrically conductive material constitutes a trigger electrode. The major surface of the cover 1008' facing the base 1006' also bears a layer of non-conductive adhesive 1020' in a first area and layer of non-conductive adhesive 1022' in a second area to bond the cover 1008' to the base 1006'.

The layers of non-conductive adhesive 1020', 1022' also function to space the cover 1008' from the base 1006' so that a channel 1024' running along the center of the sensor-portion 1002' of the test strip 1000' is formed. A layer of conductive adhesive 1026' enables the transfer of signal from the major surface 1006a' of the base 1006' to the major surface 1008b' of the cover 1008'. The layer of electrically conductive adhesive 1026' can be made from a pressure-sensitive adhesive doped with an electrically conductive material, e.g., carbon. The layer of electrically conductive adhesive 1026' typically has a thickness of about 0.002 inch.

At least one electrical passageway 1028' enables the transfer of signal from the major surface 1008b' of the cover 1008' to the major surface 1008a' of the cover 1008'. An electrical passageway 1028' is a passageway formed in the cover 1008'. The at least one electrical passageway 1028' is filled with electrically conductive material, such as, any conductive or semiconductive material described herein, for example, carbon. The benefit resulting from the use of one or more electrical passageways is that all of the contacts of the sensor-containing portion of the test strip can be positioned on one major surface of the cover of the test strip. The electrical passageways 1028' may be identical to or substantially similar to the electrical passageways 1028 shown in FIGS. 6A and 6B.

The dimensions of the sensor-containing portion 1002' of the test strip 1000' may be any suitable size, and in many embodiments the dimensions are as small as possible in order to in order to reduce the size of the assembly 110 and reduce the volume of sample required to carry out a test. For example, dimensions of the base 1006' and cover 1008' may be about 6 mm×6 mm×<2 mm. Dimensions of electrodes and channels that may be used are described in U.S. Pat. Nos. 6,229,757 and 6,616,819. When the sample of biological liquid is introduced at the sample receiving area, e.g., at hydrophilic recesses 1010' and 1012', if present, the sample is easily drawn up into the channel 1024', along which the sample flows by means of capillary attraction. The major surface of the cover 1008' not facing the base 1006' has electrical contact pads 1029a', 1029b', 1029c' exposed, which electrical contact pads 1029a', 1029b', 1029c' are in contact with the contact leads 1030a, 1030b, 1030c, 1030d of the carrier 296, as shown in FIG. 8C.

Figure 10:
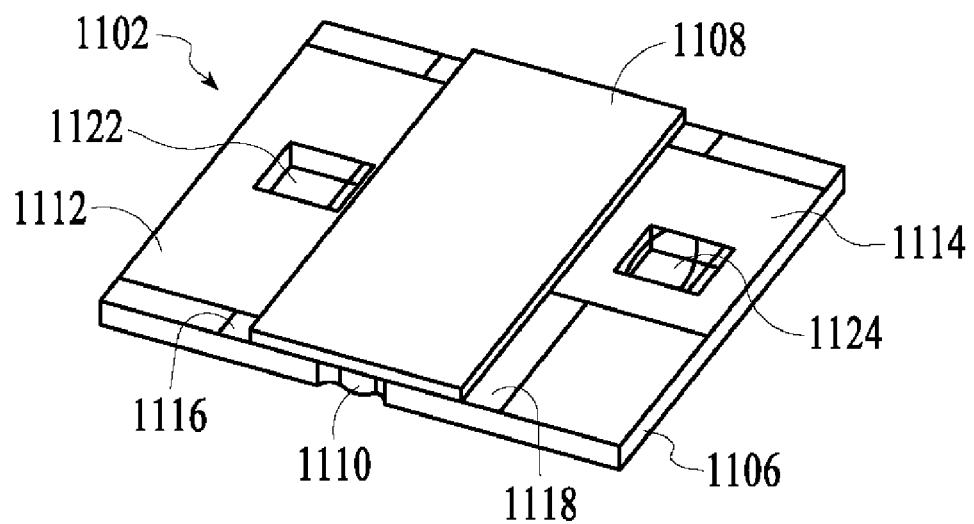
FIG. 10 illustrates a sensor containing portion of a test strip.
Figure 9:
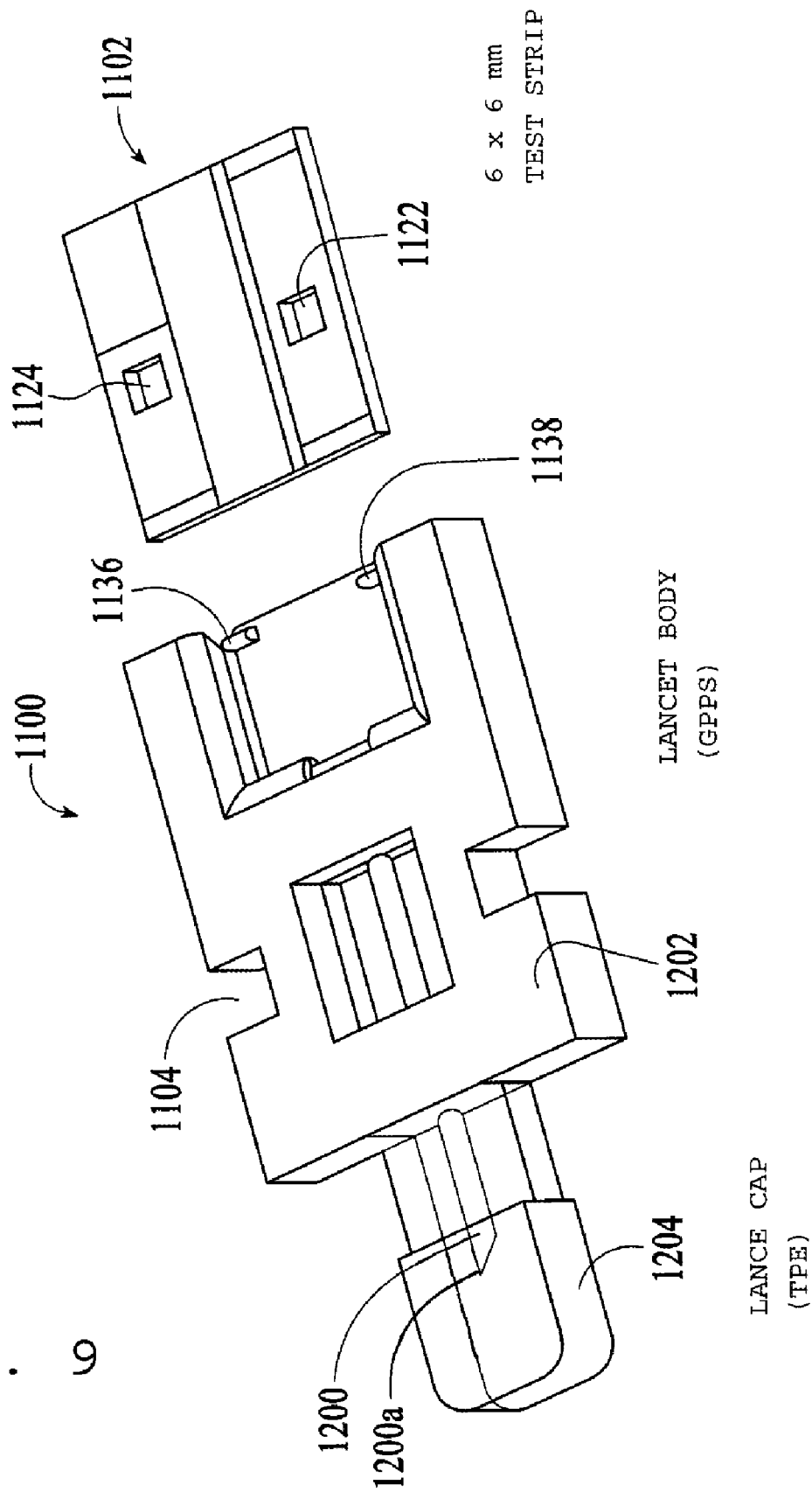
FIG. 9 is an exploded perspective view of another embodiment of the test strip, showing a lancet bearing a removable protective cover.

The base 1006' also has two openings 1032', 1034' formed therein on either side of one leg of the L-shaped electrode 1014'. The function of these openings 1032', 1034' is to securely attach the sensor-containing portion 1002' of the test strip 1000' to the lancet-containing portion, which holds the lancet in place. When the sensor-containing portion of the test strip has recesses in the sides of the cover, as shown in FIGS. 4 and 7A, the tabs of the lancet-containing portion of the test strip project downwardly, in the manner of the tabs of the lancet-containing portion shown in FIG. 4. When the sensor-containing portion of the test strip has openings in the base, as shown in FIGS. 8B, 9, and 10, the tabs of the lancet-containing portion of the test strip project upwardly, in the manner of the tabs of the lancet-containing portion shown in FIG. 9. The test strip 1000' of this embodiment can employ the same carrier 296 that can be used with the embodiment of the test strip 1000 previously described and the same type of meter as described in U.S. Pat. No. 6,616,819.

Figure 11:
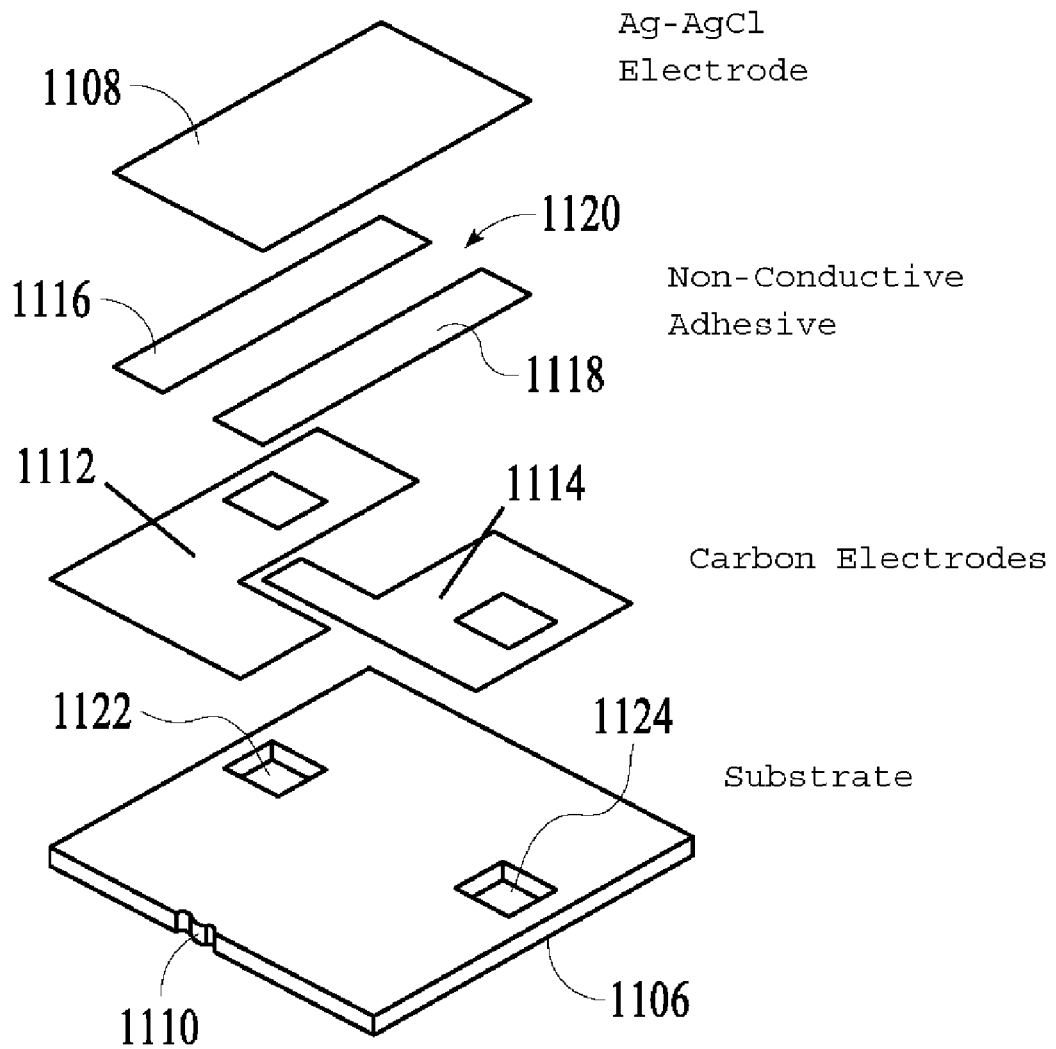
FIG. 11 is an exploded perspective view of the sensor-containing portion of the test strip shown in FIG. 9.
Figure 11:
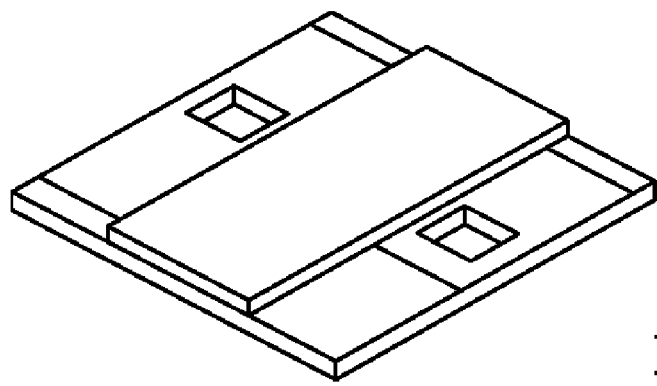

In still another embodiment, as shown in FIGS. 9-11, inclusive, a test strip 1100 comprises a sensor-containing portion 1102 and a lancet-containing portion 1104. The sensor-containing portion 1102 includes a base 1106 and a cover 1108. The base 1106 is substantially rectangular in shape and has two major surfaces 1106a, 1106b and four edges 1106c, 1106d, 1106e, and 1106f. The base 1106 has a recess 1110 formed in one edge thereof. The surface of this recess 1110 bears a hydrophilic material in order to enable the sample of biological liquid to have greater affinity for the recess 1110 than if the recess were not bearing a hydrophilic material.

On one major surface of the base 1106 is a layer of electrically conductive material 1112 in a first area and a layer of electrically conductive material 1114 in a second area. The first area constitutes the working electrode and the second area constitutes the trigger electrode. The cover 1108 is separated from the base 1106 by layers 1116, 1118 of non-conductive adhesive applied to the base 1106 and cover 1108 in such a manner that a channel 1120 forming a sample flow path is created. This channel 1120 runs along the center of the sensor-portion 1102 of the test strip 1100. The cover 1108 is made of an electrically conductive material (such as, for example, vinyl having an electrically conductive material, e.g., Ag/AgCl, thereon) and functions as a dual purpose reference/counter electrode.

When a sample of biological liquid is introduced at the hydrophilic recess 1110, the sample is easily drawn up into the channel 1116, along which the sample flows by means of capillary attraction. Portions of the electrically conductive material of the base 1106 function as electrical contact pads. The base 1106 has two openings 1122, 1124 formed therein on either side of the cover 1108. The function of these openings 1122, 1124 is to securely attach the sensor-containing portion 1102 of the test strip 1100 to the lancet-containing portion 1104, which holds the lancet in place. This embodiment does not require a conductive adhesive or electrical passageways to carry out determination of analytes.

The test strip 1100 of this embodiment can employ the same carrier 296 that can be used with the embodiments of the test strips 1000, 1000' previously described and the same type of meter as described in U.S. Pat. No. 6,616,819.

Figure 10A:
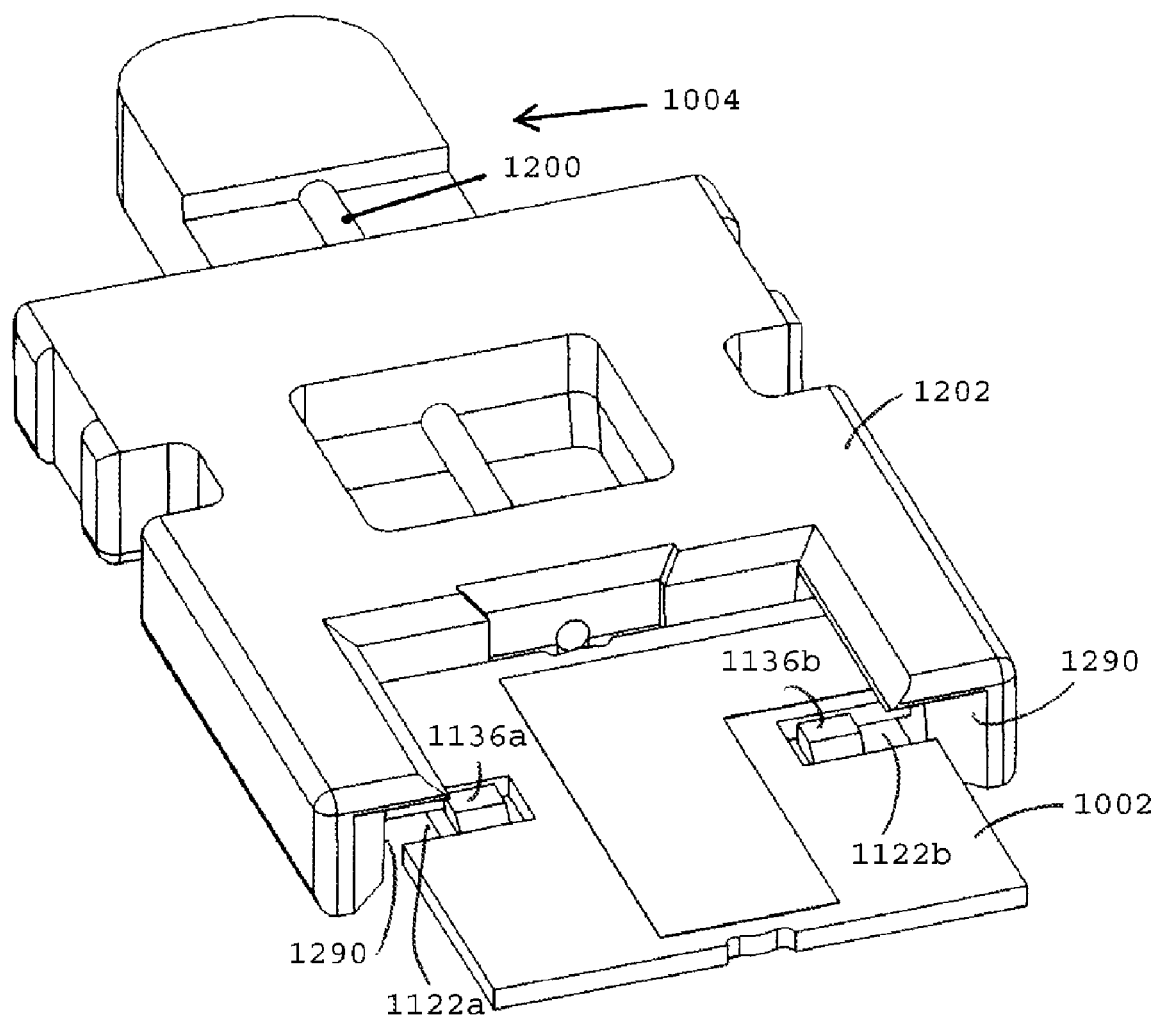
FIGS. 10A-10B illustrate a lancet body with a test strip coupled thereto and a lancet body for coupling a test strip thereto in accordance with preferred embodiments.
Figure 10B:
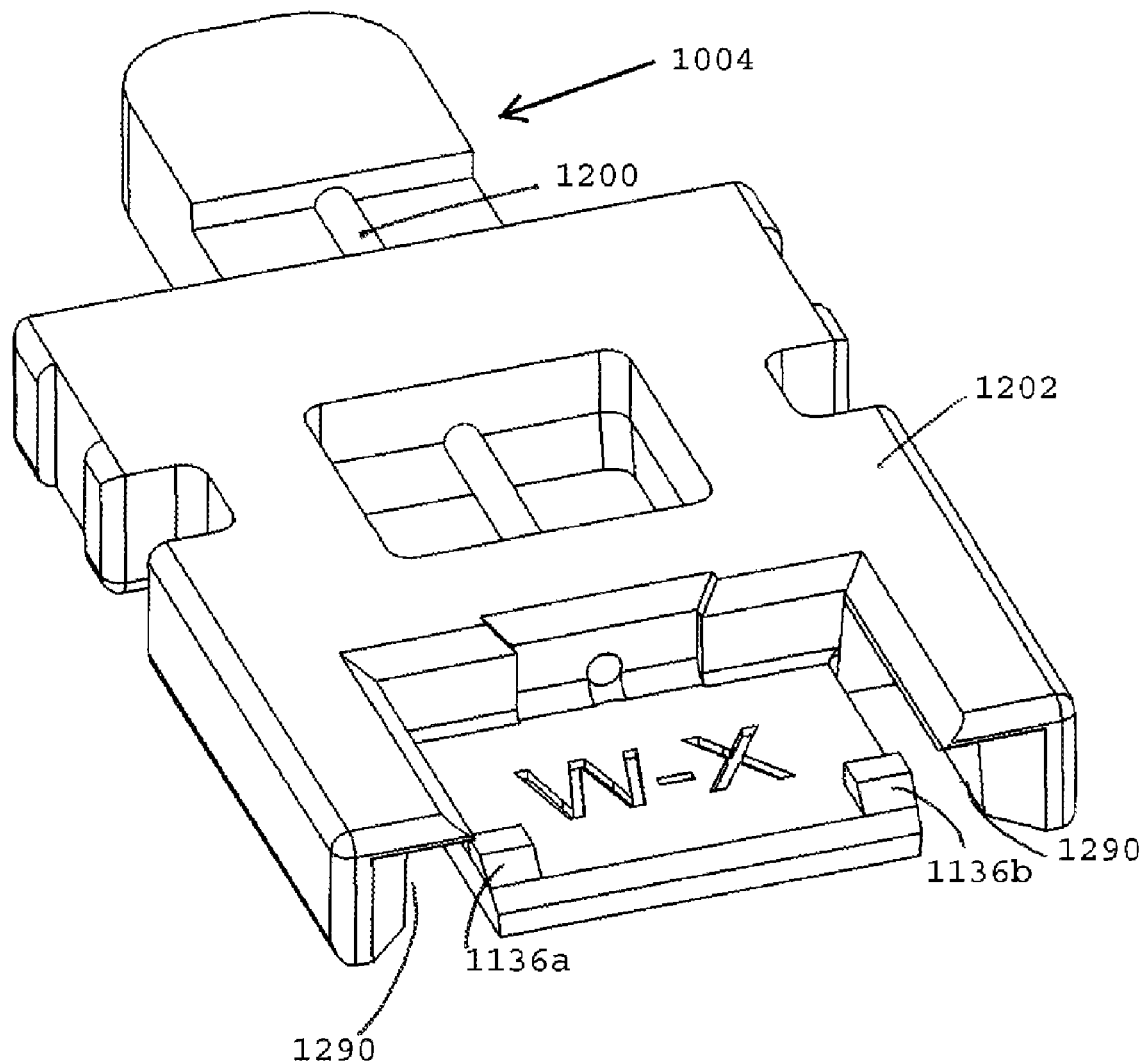

FIGS. 10A-10B illustrate embodiments of a lancet body 1202 with a test strip 1002 coupled thereto and a lancet-containing portion 1004 also coupled to the lancet body 1202 in accordance with certain embodiments. The test strip 1002 of FIG. 10A is shown with opposing rectangular cut-outs 1122a and 1122b from its sides for coupling with teeth 1136a, 1136b of the lancet body. In another embodiment which is not shown, only a single tooth and slot are involved, while rotational stabilization is provided by the configuration of the walls of the lancet body 1202. The test strip fits securely in L-shaped grooves 1290 on either side of the lancet body 1202 as illustrated at FIG. 10B.

A lancet 1200 may be integrated directly into the sensor-containing portion 1002, 1002', 1102 of the test strip. Alternatively, the sensor-containing portion 1002, 1002', 1102 of the test strip may be attached to the lancet-containing portion of the test strip. The medical diagnostic device 100 may have an alignment feature to ensure that movement, e.g., rotation, of the test strip during use does not result in misalignment of the sample application zone of the test strip. The alignment feature may be provided by springs associated with the carrier 296.

The lancet-containing portion 1004 shown in FIG. 4 may be used with, or may be modified to be used with, any of the sensor-containing portions 1002, 1002', and 1102 described herein. For example, the tabs for connecting the lancet-containing portion to the sensor-containing portion can be modified to project upwardly to enable the lancet-containing portion to be used with a sensor-containing portion having openings in the base, rather than recesses in the sides of the base and the cover. It should be noted that other embodiments of the lancet-containing portion may be used with any of the sensor-containing portions 1002, 1002', and 1102 described herein.

As shown in FIG. 4, the lancet-containing portion 1004 is shown as having a lancet-containing body 1202. The lancet 1200 is held in the lancet-containing body 1202. The lancet-containing body 1202 may be attached to the sensor-containing portion 1002 by tabs 1036, 1038 or can be attached to the sensor-containing portion 1002', 1102 by tabs 1136, 1138. When the sensor-containing portion of the test strip has recesses in the sides of the cover, as shown in FIGS. 4 and 7A, the tabs 1036, 1038 of the lancet-containing portion of the test strip project downwardly, in the manner of the tabs of the lancet-containing portion shown in FIG. 4.

When the sensor-containing portion of the test strip has openings in the base, as shown in FIGS. 8B, 9, and 10, the tabs 1136, 1138 of the lancet-containing portion of the test strip project upwardly, in the manner of the tabs of the lancet-containing portion shown in FIG. 9. Any suitable dimensions of the lancet-containing body may be employed, and in certain embodiments dimensions of the lancet-containing body 1202 of the lancet-containing portion 1004 are 10 mm×8 mm×1.5 mm. Typical dimensions of the protective cover 1204 for the lancet 1200 are 3 mm×1.4 mm. Typical dimensions of the needle for forming the lancet 1200 are 28 to 30 gauge, 10 mm total length, 3.5 mm exposed length.

A lancet 1200 for puncturing the skin to obtain a sample of biological liquid includes a sharp metal component (needle) that is maintained in a sterile condition until the moment of use. In addition, the lancet 1200 is disposable with minimum possibility of an injury subsequent to the initial use. The lancet 1200 includes a substantially cylindrical needle having a sharp end and an opposing end which may be a blunt end. The tip 1200a of the lancet 1200, i.e., the sharp end, may include a protective cover 1204 that ensures sterility of the lancet 1200. The protective cover 1204 is also designed to be re-attached to the tip 1200a of the lancet 1200 for safe disposal. The opposing end (e.g., a blunt end) may be embedded into the lancet-containing body 1202 by insert molding or adhesive. In one embodiment, the lancet-containing body 1202 includes a polymeric material molded into a substantially rectangular shape.

The tip 1200a of the lancet 1200 and as much of the lancet 1200 as is expected to puncture the skin of he patient may be embedded in the protective cover 1204, e.g., a polymeric plug, e.g., an elastomeric plug, such as a thermoplastic elastomeric, silicone, plug. In this configuration, ionizing radiation may be used to sterilize the lancet 1200 and the elastomer will prevent subsequent contamination. Embedding the piercing portion (tip) 1200a of the lancet 1200 in a soft material does not damage the delicate tip 1200a of the lancet 1200 but forms a tight seal that allows for sterilization (such as by irradiation) and the preservation of that sterile condition. Such a protective cover 1204 may be removed from the piercing portion of the lancet 1200 either by pulling the protective cover 1204 off the tip 1200a of the lancet 1200 or by fully piercing through the protective cover 1204 and allowing the protective cover 1204 to cover a more proximal part of the lancet 1200.

The nature of the thermoplastic elastomer (TPE) eliminates the necessity of relocating the tip 1200a of the used lancet 1200 precisely into the hole originally occupied by the tip 1200*a* of the unused lancet 1200. Relocation of the tip 1200*a* of the lancet 1200 at any position in the thermoplastic elastomeric protective cover 1204 is sufficient to prevent the tip 1200*a* of the lancet 1200 from being exposed after the test strip is ejected from the medical diagnostic device 100.

Thermoplastic elastomers (TPE) are easily processed rubbery materials. They can be easily formed in various shapes. If a sharp lancet 1200 is embedded into a piece of thermoplastic elastomer, and then irradiated by either gamma radiation or electron beam radiation of sufficient energy, the lancet 1200 is rendered sterile, and because the thermoplastic elastomer forms a tight seal, the lancet 1200 remains sterile for a relatively long period of time.

If the protective cover 1204 made is made of thermoplastic elastomer, and the thermoplastic elastomer is at least partially enveloped by a more rigid material, the protective cover 1204 acts more like a rigid body, but keeps the desired features of the thermoplastic elastomer. Configurations of this design might include the lamination of thermoplastic elastomer between thin layers of rigid plastic or metal or the coextrusion of thermoplastic elastomer with a more rigid polymer. The cross-section of such a coextruded profile can be circular, rectangular, or any other shape that renders it useful. Such a combination of thermoplastic elastomer and rigid material can be provided with features such that the combination is allowed to slide proximally on the shaft of the lancet 1200, eventually exposing the tip 1200*a* of the lancet 1200 for lancing. After the lancet 1200 is used, the subassembly can be slid distally and the connection between the protective cover 1204 and the lancet 1200 changed such that the protective cover 1204 cannot return to a position that exposes the tip 1200*a* of the lancet 1200.

It should be noted that all of the embodiments of the test strip shown herein are characterized by having the tip 1200*a* of the lancet 1200 of the lancet-containing portion 1004 of the test strip located about 180° from an uptake area, e.g., a recess, of the sensor-containing portion 1002, 1002', 1102 of the test strip. Such positioning renders the test strips suitable for use with the medical diagnostic device. However, the lancet may be positioned elsewhere with respect to the uptake area.

The test strips and the magazines 118 containing a plurality of test strips may be made by any suitable process. In certain embodiments, the following process may be employed:

To prepare the lancet-containing portion 1004 of a test strip, unfinished lancets are provided. These unfinished lancets are ground and cut to a suitable dimension, e.g., about 10 mm. The ground, cut lancets 1200 are then molded into a plastic body 1202 to form the lancet-containing portion 1004 of the test strip. To prepare the sensor-containing portion 1002, 1002', 1102 of the test strip, the electrodes are disposed, e.g., printed, onto the backing or cover, the appropriate reagents are disposed proximate one or more electrodes, e.g., coated over one or more of the electrodes.

Below a sample application well or zone of a test strip may be a wicking membrane that is striped with various reagents to create various reagent, capture and/or eluate zones. A hemolysis reagent zone may be positioned below a sample application zone. The hemolysis reagent zone may include a hemolysis reagent that is striped, such as absorbed, confined, or immobilized, on a wicking membrane of the test strip. A small amount of hemolysis reagent, such as about 1 to about 2 or about 3 microliters, for example, is sufficient for striping the wicking membrane such that the hemolysis reagent zone is sufficiently confined on the test strip. Any reagent or combination of reagents suitable for hemolysis, and the consequent liberation of hemoglobin, can be used. By way of example, an ionic detergent, such as sodium dodecyl sulfate (SDS), a non-ionic detergent, such as a octylphenol ethylene oxide condensate or octoxynol-9 or t-octylphenoxypolyethoxy-ethanol, sold under the name, Triton X-100, and commercially available from Sigma Chemical or Sigma-Aldrich Co., or a hypotonic solution, may be used as a hemolysis reagent.

A glycated hemoglobin capture zone may be disposed downstream relative to the hemolysis zone. By way of example, any chemical reagent comprising at least one boron ligand, such as phenyl boronate or other boron affinity chemistry used in the above-referenced Glycosal test, or such as m-aminophenylboronic acid, such as that of a gel that is immobilized on cross-linked, beaded agarose, any antibody, such as anti-HbA1c antibody available from a number of sources, any immunoassay reagent, any chemical reagent including at least one binding ligand, such a boronic acid involving boron binding ligands, and the like, and any combination thereof, that is suitable for the binding of glycated hemoglobin to the capture zone 222, such as via covalent bonds, for example, or the capture of glycated hemoglobin in capture zone 222, may be used. A hemolysis layer/zone and a glycated hemoglobin capture zone can be integrated to form an integrated reagent zone.

The cards of sensor-containing portions 1002, 1002', 1102 are singulated to form individual sensor-containing portions 1002, 1002', 1102. The individual sensor-containing portions 1002, 1002', 1102 are combined with the lancet-containing portions 1004 to form completed test strips. Pluralities of test strips are then loaded into assembly 110 (see FIG. 1).

The sensors described herein may be configured for analysis of an analyte in a small volume of sample by, for example, coulometry, amperometry, and/or potentiometry. The sensors may also be configured for optical analysis. The sensors may be configures to determine analyte concentration in about 1 µL or less of sample, e.g., 0.5 µL or less of sample e.g., 0.2 µL or less of sample e.g., 0.1 µL or less of sample. The chemistry of the sensors generally includes an electron transfer agent that facilitates the transfer of electrons to or from the analyte. One example of a suitable electron transfer agent is an enzyme which catalyzes a reaction of the analyte. For example, a glucose oxidase or glucose dehydrogenase, such as pyrroloquinoline quinone glucose dehydrogenase (PQQ), may be used when the analyte is glucose. Other enzymes may be used for other analytes. Additionally or alternatively to the electron transfer agent, may be a redox mediator. Certain embodiments use a redox mediator that is a transition metal compound or complex. Examples of suitable transition metal compounds or complexes include osmium, ruthenium, iron, and cobalt compounds or complexes. In these complexes, the transition metal is coordinatively bound to one or more ligands, which are typically mono-, di-, tri-, or tetradentate. The redox mediator may be a polymeric redox mediator or a redox polymer (i.e., a polymer having one or more redox species). Examples of suitable redox mediators and redox polymers are disclosed in U.S. Pat. Nos. 6,338,790; 6,229,757; 6,605,200 and 6,605,201.

The senor also includes a sample chamber to hold the sample in electrolytic contact with the working electrode. In certain embodiments, the sample chamber may be sized to contain no more than about 1 µL of sample, e.g., no more than about 0.5 µL, e.g., no more than about 0.2 µL, e.g., no more than about 0.1 µL of sample.

U.S. Pat. No. 6,229,757 also discloses materials for preparing a working electrode, a counter electrode, a dual purpose reference/counter electrode, a reference electrode, analytes that may be determined, examples of redox mediators, examples of second electron transfer agents, and details of sample chamber. The teachings of U.S. Pat. No. 6,299,757 may be used to prepare the components of the sensor-containing portion of the test strips.

The assemblies 110 of FIG. 1 may be prepared by first molding the desiccants into platforms. Resilient biasing elements and the platforms are then assembled into the housings of the assemblies 110. The assemblies 110 are then packed and shipped.

Operation

Figure 12:
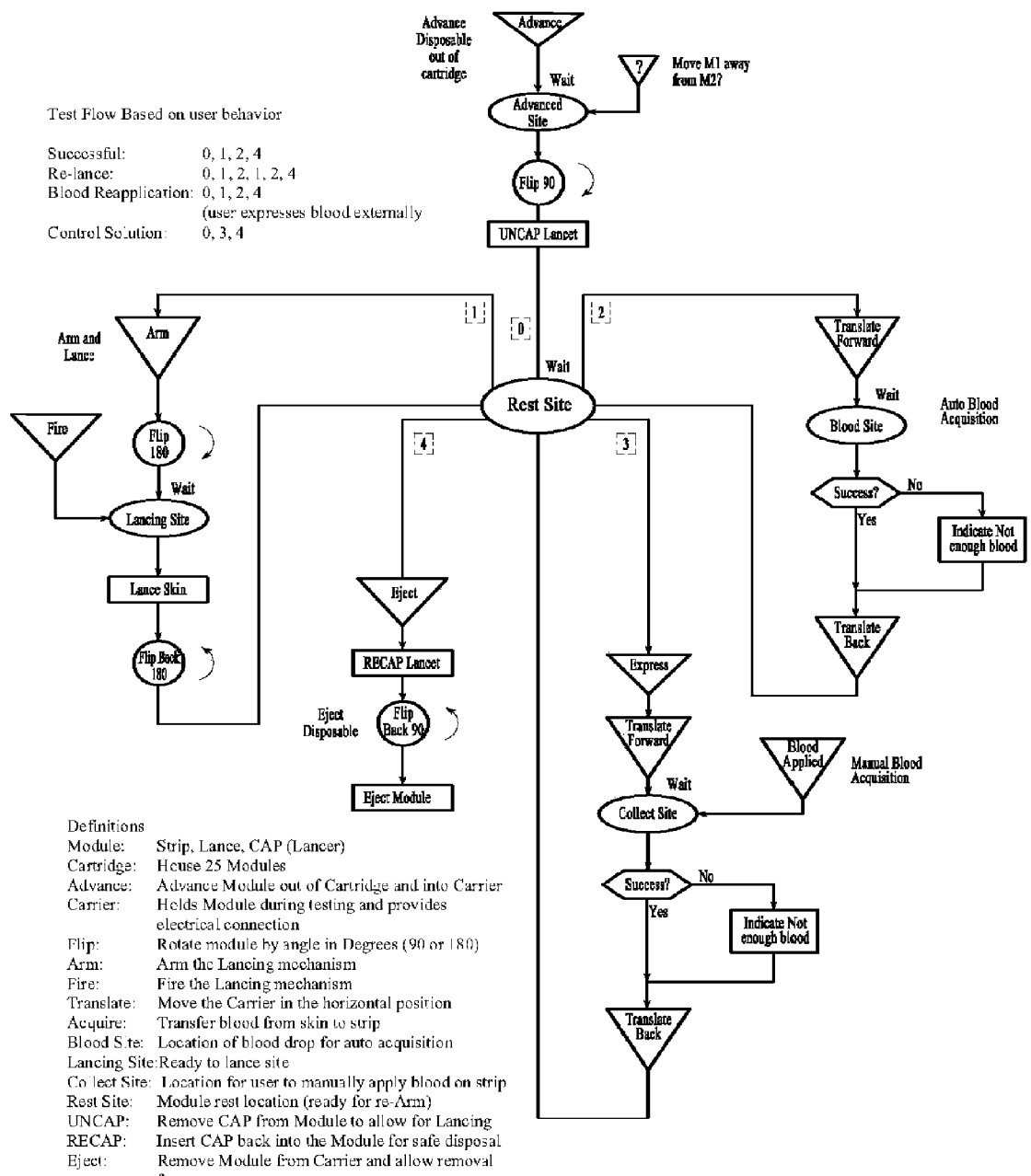
FIG. 12 is a flow chart illustrating the operations of a medical diagnostic device involving an integrated lancet and testing striplet in accordance with a preferred embodiment.

Embodiments for operating the medical diagnostic device to dispense a test strip, form an opening in the skin of a patient to obtain a sample of biological liquid, collect a sample of biological liquid from the patient, analyze the sample of biological liquid collected from the patient, and dispose of the used test strip will now be summarized. FIG. 12 also depicts operational processes in a flow chart for certain embodiments. Embodiments may include fewer than all of that which is shown, and other may include further processes.

After the test strip 1000 has been fed into the cradle 280, the medical diagnostic device 100 causes the test strip 1000 to be oriented in such a manner that the lancet 1200 of the lancet-containing portion 1004 of the test strip 1000 may be introduced into the skin of a patient to form an opening in the skin of the patient. In certain embodiments, such an orientation is carried out by a motor. In these embodiments, a PCB assembly may be programmed so that orientation is carried out accurately and reliably.

Such an orientation may be carried out by having the transmission system rotate the cradle 280 of the lancing/collecting assembly, e.g., about 90° (clockwise or counterclockwise), so that the tip 1200a of the lancet 1200 faces an opening in an end cap, so that when the medical diagnostic device 100 is placed against the skin of the patient, the tip 1200a of the lancet 1200 will be facing the skin of the patient.

The medical diagnostic device 100 then causes the test strip 1000 to be oriented in such a manner that the sensor-containing portion 1002 of the test strip 1000 may be placed in contact with the sample of biological liquid emerging from the opening in the skin of the patient. For this step, the cradle 280 is rotated about 180° in certain embodiments so that the sensor-containing portion 1002 of the test strip 1000 contacts, e.g., directly overlies, the biological liquid.

The sample of biological liquid enters the sample application zone of the sensor-containing portion 1002 of the test strip 1000, i.e., the recesses 1010, 1012 formed in an edge of the test strip 1000. The sample of biological liquid travels along the sample flow channel 1024 to the area where the reagents are disposed. The appropriate reaction occurs, thereby activating the electronics and bringing about a reading of the concentration of the analyte, which reading is shown in the display. If insufficient quantity of the sample of biological liquid is drawn in the initial lancing, the user can actuate a retesting procedure before actuating the analyzing, whereby the test is aborted so that the user can re-arm the lancing mechanism and begin again.

The sensor-containing portion 1002 of the test strip 1000 collects a sufficient quantity of sample of biological liquid to allow analysis of the sample of biological liquid. After a sufficient amount of sample of biological liquid is collected, the carrier 296, the electrical components of which are in electrical contact with the contacts of the sensor-containing portion 1002 of the test strip 1000, measures the quantity of analyte in the sample by an electrochemical analyzer. By this process, the sample of biological liquid is analyzed to determine at least one characteristic of the sample of biological liquid.

After the sample of biological liquid is analyzed, the protective cover if provided 1204 is automatically re-attached to the tip 1200a of the lancet 1200 of the lancet-containing portion 1004 of the test strip 1000. After the protective cover 1204 is re-attached, the re-covered test strip 1000 is ejected from a port in the housing (not shown), e.g., automatically.

FIG. 12 is a flow chart that illustrates embodiments of a method in accordance with certain embodiments. As shown in FIG. 12, in this embodiment there are five basic components of the method. Component 0 of FIG. 12 involves advancing the test strip from the assembly 110 into the cradle 280, removing the protective cover 1204 from the lancet 1200, and rotating the cradle 280 to position the lancet 1200 for entering the skin of the patient. It should be noted that the protective cover 1204 could be removed from the lancet 1200 prior to rotating the cradle 280 into position for lancing. Component 1 of FIG. 12 involves arming and triggering the lancet 1200. Component 2 of FIG. 12 involves indexing the test strip so that the sensor portion of the test strip can obtain blood from the opening formed in the skin in Component 1. Component 3 of FIG. 12 involves collecting blood from the opening formed in the skin in Component 1. Component 4 of FIG. 12 involves reattaching the protective cover 1204 to the lancet 1200 and ejecting the used test strip from the medical diagnostic device 100.

FIG. 13A through FIG. 13M, inclusive, illustrate in schematic form one way of carrying out the method of FIG. 12. For the sake of simplification, the test strip will be the test strip shown in FIG. 4. Other test strips described can be used in place of the test strip shown in FIG. 4. FIG. 13A shows a test strip 1000 in the assembly 110. FIG. 13B shows the test strip 1000 advanced from the assembly 110 and inserted into the lancing/collecting assembly, which is represented schematically by two parallel upright elements, each element having a slot formed therein. FIG. 13C shows the protective cover 1204 being removed from the lancet 1200 of the test strip 1000. It should be noted that the protective cover 1204 could be removed before the test strip 1000 is inserted into the lancing/collecting assembly.

FIG. 13D shows the test strip 1000 rotated about 90° so that the lancet 1200 is in position for lancing the skin of the patient. FIG. 13E shows that the lancet 1200 has entered the skin of the patient. FIG. 13F shows that the lancet 1200 has been retracted from the skin of the patient. FIG. 13G shows that the test strip 1000 is being rotated about 180° so that the sensor-containing portion 1002 can collect biological liquid emerging from the opening formed in the skin of the patient. FIG. 13H shows that the sensor-containing portion 1002 of the test strip 1000 is ready to be indexed so that the sensor-containing portion 1002 can collect biological liquid emerging from the opening formed in the skin of the patient.

FIG. 13I shows the sensor-containing portion 1002 of the test strip 1000 contacting the biological liquid emerging from the skin of the patient. FIG. 13J shows that the test strip 1000 is being rotated about 90° so that the test strip 1000 will come into the proper in position for being ejected from the medical diagnostic device. FIG. 13K shows the test strip 1000 in position for ejection from the medical diagnostic device 100. FIG. 13L shows the protective cover 1204 being reattached to the lancet 1200. FIG. 13M shows the test strip 1000 being ejected from the medical diagnostic device 100.

Alternative Embodiments

The monitoring apparatuses are configured for analysis (e.g., concentration determination) of an analyte in a sample of body fluid, where in certain embodiments the apparatuses are configured to determine the concentration of an analyte in a small volume of sample, e.g., less than about 1 microliter, e.g., less than about 0.5 microliters, e.g., less than about 0.2 microliters, e.g., about 0.1 microliters or less. The monitoring apparatuses may be configured for analysis of an analyte in a volume of sample by, for example, coulometry, amperometry, and/or potentiometry. In certain embodiments, the monitoring apparatuses are configured for optical analysis of an analyte in a sample.

A striplet includes both a test strip portion and a lancet portion. These may be relatively opposed, e.g., extending about 180 degrees from each other, or extending at another angle from zero to 360 degrees. The lancet portion may couple to the test strip portion as a two-piece device, or each may couple with a lancet body as a three-piece device.

In an alternative embodiment, a medical diagnostic device is provided that carries out the functions of:

(f) storing a plurality of lancets and sensors;
(g) feeding a plurality of lancets and sensors to a system that employs a lancet to form an opening in the skin of a patient and then employs the sensor to collect a sample of biological liquid that emerges from the opening formed in the skin;
(h) forming an opening in the skin of the patient by means of the lancet;
(i) collecting the sample of biological liquid emerging from the opening formed in the skin of the patient by means of the sensor;
(j) analyzing the sample of biological liquid collected by the sensor; and
(k) ejecting the used lancet and the used sensor in a safe manner.

In a further embodiment, a test strip includes a lancet-containing portion and a sensor-containing portion. During the time that the test strip is stored in the medical diagnostic device, a protective cover encloses the lancet of the lancet-containing portion. The medical diagnostic device is capable of removing the protective cover to enable the lancet to form an opening in the skin of the patient and is further capable of re-attaching the protective cover onto the lancet to enable the medical diagnostic device to eject the used test strip in a safe manner.

In another embodiment, a lancing/collecting assembly receives a test strip that includes both a lancet-containing portion and a sensor-containing portion. By means of various operations, the lancing/collecting assembly is configured to (a) orient the lancet-containing portion of the test strip in such a manner that the lancet of the lancet-containing portion of the test strip can be advanced toward a lancing and testing site on the skin of the patient in order to form an opening therein, (b) arm the lancet of the lancet-containing portion of the test strip, (c) trigger the armed lancet of the lancet-containing portion of the test strip so that the lancet forms an opening in the skin of the patient at the lancing and testing site, (d) orient the sensor-containing portion of the test strip in such a manner that the sensor-containing portion of the test strip can be advanced toward the opening formed in the skin of the patient to collect a sample of biological liquid emerging from the opening in the skin of the patient at the lancing and testing site which remains proximate to a lancing and testing port of an analyte, e.g., glucose, monitoring apparatus; and (e) advance the sensor of the sensor-containing portion of the test strip so that sufficient quantity of the sample of biological liquid can be collected for analysis to determine a parameter of the biological liquid, e.g., a body analyte, e.g., glucose, level.

The lancing/collecting assembly may also incorporate an analyzer that is capable of analyzing the sample of biological liquid collected from the opening in the skin of the patient.

In another embodiment, a storing/dispensing assembly is provided for a plurality of test strips, each of which includes a lancet-containing portion and a sensor-containing portion.

In a further embodiment, a method for using a medical diagnostic device includes:

(a) feeding one of multiple test strips, each of the test strips having a lancet-containing portion and a sensor-containing portion, to a lancing/collecting assembly that employs a lancet of the lancet-containing portion to form an opening in the skin of a patient, and then employs a sensor of the sensor-containing portion to collect a sample of biological liquid that emerges from the opening formed in the skin;
(b) forming an opening in the skin of the patient by means of a lancet in the lancet-containing portion;
(c) collecting a sample of biological liquid emerging from the opening formed in the skin of the patient by means of the sensor of the sensor-containing portion;
(d) analyzing the sample of biological liquid collected by the sensor of the sensor-containing portion; and
(e) ejecting the used test strip in a safe manner.

A medical diagnostic device of an embodiment can perform a plurality of diagnostic tests, e.g., 25 tests, before the device requires refilling with test strips. The medical diagnostic device can perform the functions of storing and dispensing test strips, lancing the skin of a patient, collecting a sample of biological liquid, analyzing the sample of biological liquid collected, and disposing of used test strips. In the case of collection of an inadequate quantity of sample, the medical diagnostic device enables re-lancing.

In accordance with another embodiment, a medical diagnostic device requires only a small volume of sample to carry out a complete test, e.g., 0.3 microliter (see, e.g., U.S. Pat. Nos. 7,058,437, 6,618,934, 6,591,125 and 6,551,494, which are hereby incorporated by reference).

The test strip combines a lancet and a sensor in a single small unit. After the skin of the patient is pierced and a sample of biological liquid, e.g., blood, appears, the test strip is moved into position for collecting a sample of the liquid, and the liquid enters the sample application zone of the sensor-containing portion of the test strip without manipulation of the test strip by the user.

The striplet is also small in size. Generally the striplet is less than 2 mm×less than 1 mm×less than 0.3 mm, and in some embodiments, less than 1.5 mm×less than 0.75 mm×less than 0.2 mm, e.g., approximately 1 mm×0.5 mm×0.1 mm.

The striplet is advantageously ideal for alternative site testing, i.e., away from the fingertips, where smaller amount of blood are available than at the fingertips, such as less than 1 microliter, and even less than 0.5 microliters, or less than 0.3 microliters, or less than 0.2 microliters, or even 0.1 microliters (100 nanoliters). See for example U.S. Pat. No. 6, 284, 125 which describes this feature in more detail and in incorporated by reference.

Embodiments include calibration in one or more schemes. A calibration module, whether it be a bar code, a RFID tag, a label, or otherwise may be located on a striplet and/or on a striplet container. U.S. application Ser. No. 11/350,398, which is assigned to the same assignee and incorporated by reference, provides further examples. There may be contact pads that may be shorted together or kept apart during the test strip manufacturing process in order to communicate a calibration code to the meter. There may be a set of contact pads and a varying resistance between the two pads where the resistance is changed during the manufacturing process of the test strip to communicate a calibration code to the meter. There may be an electrical memory that is readable and writable by the meter, which communicates a calibration code to the meter. A calibrator can carry other information such as striplet expiration and/or a striplet number count down.

Various modifications and alterations of this invention will become apparent to those skilled in the art without departing from the scope and spirit of this invention, and it should be understood that this invention is not to be unduly limited to the illustrative embodiments set forth herein, which may be amended or modified or elements thereof combined without departing from the scope of the present invention, which is as set forth in the appended claims including structural and functional equivalents thereof.

In methods that may be performed according to embodiments herein and that may have been described above and/or claimed below, the operations have been described in selected typographical sequences. However, the sequences have been selected and so ordered for typographical convenience and are not intended to imply any particular order for performing the operations. Additionally, some parts of a sequence may be omitted and/or added in certain embodiments.

In addition, all references cited above herein, in addition to the background and summary of the invention section, are hereby incorporated by reference into the detailed description of the embodiments as disclosing alternative embodiments and components.

What is claimed is:

1. A method of providing a sample of body fluid to a test strip for measuring an analyte level within the fluid, comprising:
    providing an integrated lancing and testing strip including a lancet needle and a test strip that are coupled at opposite ends of a lancet body of the integrated lancing and testing strip, the test strip having a flat substrate including first and second major surfaces and edge surfaces, wherein the first and second major surfaces are larger than the edge surfaces, and wherein the first major surface faces a first orthogonal direction;
    loading the integrated lancing and testing strip within an analyte meter including arming the lancet needle by removing a lancet cap;
    piercing a lancing site with the lancet needle at a predetermined location relative to the meter; and
    automatically reorienting the integrated lancing and testing strip within the analyte meter such that the first major surface faces a second orthogonal direction; and
    automatically advancing and contacting a sample receiving portion of the test strip at the lancing site, such that body fluid from the lancing site is automatically applied to the sample receiving portion of the test strip for measuring an analyte level.

2. The method of claim 1, further comprising disarming the lancet needle and disposing of the integrated lancing and testing strip.

3. The method of claim 1, wherein the lancing site remains approximately at said predetermined location relative to the meter when body fluid is applied to the sample receiving portion of the test strip.

4. The method of claim 1, wherein the loading comprises mating a first recess defined within the lancet body with a latching mechanism of the analyte meter, such that the integrated lancing and testing strip is specifically disposed at a lancing orientation.

5. The method of claim 4, wherein the flipping comprises mating a second recess defined within the lancet body with the same latching mechanism, such that the integrated lancing and testing strip is specifically disposed at a testing orientation.

6. The method of claim 5, wherein each of said pair of recesses comprises a trapezoidal shape.

7. The method of claim 6, wherein the loading comprises mating a first recess defined within the lancet body with a spring-loaded ball and detent mechanism of the analyte meter, such that the integrated lancing and testing strip is specifically disposed at a lancing orientation.

8. The method of claim 7, wherein the flipping comprises mating a second recess defined within the lancet body with the same ball and detent mechanism, such that the integrated lancing and testing strip is specifically disposed at a testing orientation.

9. The method of claim 1, wherein the lancing site remains approximately at said predetermined location relative to the meter when body fluid is applied to the sample receiving portion of the test strip, and wherein the test strip and lancet are symmetrically disposed at opposite ends of the lancet body.

10. The method of claim 9, wherein the loading comprises mating a first recess defined within the lancet body with a ball and detent mechanism of the analyte meter, such that the integrated lancing and testing strip is specifically disposed at a lancing orientation.

11. The method of claim 10, wherein the flipping further comprises mating a second recess defined within the lancet body symmetrically opposite the first recess with the same ball and detent mechanism, such that the integrated lancing and testing strip is specifically disposed at a testing orientation.

12. The method of claim 11, wherein the loading comprises mating a first recess defined within the lancet body with a latching mechanism of the analyte meter, such that the integrated lancing and testing strip is specifically disposed at a lancing orientation.

13. The method of claim 12, wherein the flipping further comprises mating a second recess defined within the lancet body symmetrically opposite the first recess with the same latching mechanism, such that the integrated lancing and testing strip is specifically disposed at a testing orientation.

14. The method of claim 1, wherein the arming comprises uncoupling a lancet cap by uncoupling one or more elastomeric arms of the lancet cap from defined cutouts in the lancet body by application of sufficient separating force.

15. The method of claim 14, further comprising disarming the lancet needle, including snapping the one or more elastomeric arms of the lancet cap back into mating relationship with the defined cutouts of the lancet body by application of sufficient coupling force.

16. The method of claim 1, further comprising coupling at least one tooth that fits a corresponding slot, and rotationally stabilizing the test strip relative to the lancet body, for coupling the lancet body and test strip together.

17. The method of claim 1, further comprising coupling at least two teeth that fit corresponding slots for coupling the lancet body and test strip together.

18. The method of claim 17, wherein the lancet body comprises said teeth and the test strip comprises said corresponding slots.

* * * * *